US008796206B2

(12) United States Patent
Sloey et al.

(10) Patent No.: US 8,796,206 B2
(45) Date of Patent: Aug. 5, 2014

(54) AQUEOUS FORMULATION OF ERYTHROPOIESIS STIMULATING PROTEIN STABILISED BY ANTIOXIDANTS FOR PARENTERAL ADMINISTRATION

(75) Inventors: Christopher James Sloey, Newbury Park, CA (US); Jason Ko, Thousand Oaks, CA (US); Tiansheng Li, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 1 day.

(21) Appl. No.: 12/743,333

(22) PCT Filed: Nov. 13, 2008

(86) PCT No.: PCT/US2008/083327
§ 371 (c)(1),
(2), (4) Date: Aug. 6, 2010

(87) PCT Pub. No.: WO2009/064838
PCT Pub. Date: May 22, 2009

(65) Prior Publication Data
US 2010/0297117 A1 Nov. 25, 2010

Related U.S. Application Data

(60) Provisional application No. 60/988,354, filed on Nov. 15, 2007.

(51) Int. Cl.
*A61K 38/18* (2006.01)
*C07K 14/505* (2006.01)

(52) U.S. Cl.
USPC .......................................... 514/7.7; 530/399

(58) Field of Classification Search
None
See application file for complete search history.

(56) References Cited

U.S. PATENT DOCUMENTS

| | | | |
|---|---|---|---|
| 4,687,761 A | 8/1987 | Liu | 514/26 |
| 4,842,859 A | 6/1989 | Liu | 424/736 |
| 4,888,354 A | 12/1989 | Chang et al. | 514/424 |
| 5,254,339 A | 10/1993 | Morein | 424/191.1 |
| 5,350,741 A | 9/1994 | Takada | 424/85.2 |
| 5,362,494 A * | 11/1994 | Zysman et al. | 424/401 |
| 5,364,839 A | 11/1994 | Gerhart et al. | 514/8.2 |
| 5,631,294 A | 5/1997 | Kurtz et al. | 514/568 |
| 5,661,125 A | 8/1997 | Strickland | 514/7.7 |
| 5,932,194 A | 8/1999 | Plessix et al. | 424/59 |
| 6,083,921 A | 7/2000 | Xu | 514/26 |
| 6,107,281 A | 8/2000 | Jones et al. | 514/3.7 |
| 6,113,909 A | 9/2000 | Han et al. | 424/775 |
| 6,284,749 B1 | 9/2001 | Castillo et al. | 514/159 |
| 6,303,113 B1 * | 10/2001 | Woog et al. | 424/85.1 |
| 6,387,461 B1 | 5/2002 | Schnittger et al. | 514/461 |
| 6,423,680 B1 | 7/2002 | Rigat et al. | 514/20.6 |
| 6,495,120 B2 | 12/2002 | McCoy et al. | 424/45 |
| 6,524,625 B2 | 2/2003 | Aga et al. | 424/725 |
| 6,632,459 B2 | 10/2003 | Graus et al. | 424/728 |
| 6,696,056 B1 | 2/2004 | Cheung et al. | 424/85.1 |
| 6,696,089 B2 | 2/2004 | Kabanov et al. | 424/484 |
| 6,746,666 B1 | 6/2004 | Luther | 424/59 |
| 6,858,235 B2 | 2/2005 | Park et al. | 424/765 |
| 6,960,617 B2 | 11/2005 | Omidian et al. | 521/102 |
| 6,989,164 B2 | 1/2006 | Trant | 424/729 |
| 6,989,262 B2 | 1/2006 | Bejanin et al. | 435/226 |
| 7,001,892 B1 * | 2/2006 | Chmielewski et al. | 514/53 |
| 7,005,539 B2 | 2/2006 | Yu et al. | 562/400 |
| 7,790,679 B2 * | 9/2010 | Li et al. | 514/7.7 |
| 2002/0094948 A1 * | 7/2002 | Lehmann | 514/2 |
| 2003/0104996 A1 * | 6/2003 | Li et al. | 514/12 |
| 2003/0203857 A1 * | 10/2003 | Ohnogi et al. | 514/27 |
| 2004/0091388 A1 * | 5/2004 | MacPhee et al. | 422/22 |
| 2005/0281772 A1 * | 12/2005 | Bromley et al. | 424/70.14 |
| 2006/0051435 A1 | 3/2006 | Udell et al. | |
| 2006/0073563 A1 * | 4/2006 | Marshall | 435/69.1 |
| 2006/0204596 A1 | 9/2006 | Jia et al. | |
| 2006/0247274 A1 | 11/2006 | Connolly et al. | |
| 2009/0240029 A1 * | 9/2009 | Miao et al. | 530/329 |
| 2010/0028372 A1 * | 2/2010 | Jezek | 424/184.1 |
| 2010/0316593 A1 * | 12/2010 | Li et al. | 424/85.1 |
| 2011/0052532 A1 * | 3/2011 | Strobl et al. | 424/85.2 |

FOREIGN PATENT DOCUMENTS

| | | |
|---|---|---|
| WO | 03020299 | 3/2003 |
| WO | 2004108152 | 12/2004 |
| WO | WO 2006/073461 | * 7/2006 |
| WO | WO 2006/125762 | * 11/2006 |
| WO | 2007037795 | 4/2007 |
| WO | 2008084237 | 7/2008 |

OTHER PUBLICATIONS

Boissel et al. Erythropoietin structure-function relationships. Mutant proteins that test a model of tertiary structure. The Journal of Biological Chemistry, vol. 268, No. 21:15983-15993 (1993).*
Chern et al. Structural role of amino acids 99-110 in recombinant erythropoietin. European Journal of Biochemistry, vol. 202:225-229 (1991).*
Giacomelli et al. Antioxidant activity of phenolic and related compounds: a density functional theory study on the O-H bond dissociation enthalpy; Redox Report, vol. 9/5:263-269 (2004).*
Arunachalam et al. Biodegradation of catechin. Proceedings of the Indian National Science Academy Part B Biological Sciences, Abstract vol. 69, No. 4, pp. 353-370 (Aug. 2003).*
Abdelwahed et al., "Study of antimutagenic and antioxidant activities of Gallic acid and 1,2,3,4,6-pentagalloylglucose from *Pistacia lenticus* confirmation by microarray expression profiling," *Chemico-Biological Interactions* 165, 1-13 (2007).
Egrie et al., "Development and characterization of novel erythropoiesis stimulating protein (NESP)," *British Journal of Cancer* 84: 3-10, (2001).
Naczk et al., "Extraction and analysis of phenolics in food," *J. Chromatogr.A* 1054: 95-111 (2004).
Potier, et al., "Gallic Esters of Sucrose as a New Class of Antioxidants," *Tetrahedon Letters* 40: 3387-3390 (1999).
International Search Report in corresponding PCT/US2008/083327 dated Apr. 15, 2009, pp. 1-12.
Written Opinion in corresponding PCT/US2008/083327 dated Apr. 15, 2009, pp. 1-8.
International Preliminary Report on Patentability in corresponding PCT/US2008/083327 dated May 18, 2010, pp. 1-9.

* cited by examiner

*Primary Examiner* — Elizabeth C Kemmerer
*Assistant Examiner* — Regina M Deberry
(74) *Attorney, Agent, or Firm* — Marshall, Gerstein & Borun LLP

(57) ABSTRACT

The present invention relates to stable aqueous protein formulations. In particular, disclosed herein are therapeutic protein formulations suitable for parenteral administration having one or more antioxidants.

8 Claims, 29 Drawing Sheets

AQUEOUS FORMULATION OF ERYTHROPOIESIS STIMULATING PROTEIN STABILISED BY ANTIOXIDANTS FOR PARENTERAL ADMINISTRATION

CROSS-REFERENCE TO RELATED APPLICATIONS

This patent application is the U.S. national stage of PCT/US2008/083327 filed Nov. 13, 2008 and which claims the benefit of U.S. Provisional Patent Application No. 60/988,354, filed on Nov. 15, 2007, both of which are incorporated by reference.

FIELD OF THE INVENTION

The present invention relates to stable aqueous pharmaceutical formulations of therapeutic proteins. In particular, the present invention relates to aqueous pharmaceutical formulations of therapeutic proteins suitable for parenteral administration that comprise an antioxidant.

BACKGROUND OF THE INVENTION

Therapeutic proteins may at times during the course of manufacturing, handling, storage, and administration be exposed to visible light and ultraviolet radiation. Protecting proteins from light exposure has typically involved physically covering the sample with foil, or a box or other container, or by storage in a closed refrigerator. There may be times, however, when exposure of the protein to light may be unavoidable and as a result of this exposure, the protein may become degraded. Light induced degradation of proteins can involve the oxidation of several amino acids including tryptophan, tyrosine, methionine, histidine, and cysteine. If the oxidation alters the protein's structural properties, it may lose biological activity. The oxidation of certain amino acid residues may also lead to yellowing of the protein solution. Moreover, the oxidized protein may aggregate through disruption of native disulfide bonds or through the formation of dityrosine linkages. The loss of biological activity, change in color and/or clarity of the protein solution, and formation of aggregates are commercially undesirable effects. In extreme cases the oxidation or aggregation could cause an immunogenic response in patents with possibly severe side effects.

In addition to free radicals generated by light exposure, proteins may be formulated with excipients containing small amounts of impurities which, although harmless themselves, could generate free radicals that hasten degradation and/or oxidation of proteins. Protein formulations in pre-filled syringes and other drug delivery devices may contain extractables or metal ions which could catalyze free radical generation and protein oxidation. Approved excipients for use in protein formulation may be limited in their ability to prevent these types of oxidation.

Various types of molecules such as sugars, surfactant, amino acids and fatty acids have been used in efforts to stabilize protein and peptide products against degradation. See Wang and Hanson, J. Parenteral Science and Technology Supplement, 1988, Technical Report No. 10 (describing parenteral formulations of proteins and peptides); Manning et al., 6 Pharmaceutical Research, 1989. Examples of excipients such as buffers, preservatives, isotonic agents, and surfactants are also known in the art. See 21 C.F.R.sctn.180.22 et seq. (defining recognized food additives); Wang and Kowal, 34 J. Parenteral Drug Association 452, 1980 (describing various excipients); A. R. Gennaro et al., 17th Remington's "Pharmaceutical Sciences." 1985; Avis et al., Pharmaceutical Dosage Forms: Parenteral Medications, Vol. 1, 1992, all of which, including the definitions of various useful excipients, are hereby incorporated by reference herein.

It is understood that the development of a suitable aqueous formulation for administration to a subject is complex. A need exists in the art for aqueous formulations of therapeutic proteins having minimal physical and chemical degradation when exposed to varying levels of UV radiation or other light, or when exposed to other sources that generate free radicals.

SUMMARY OF THE INVENTION

The present invention is directed toward aqueous pharmaceutical formulations of pharmaceutically active proteins and antioxidants that exhibit superior stability and/or resistance to oxidation or degradation induced by free radicals, methods of preparing such formulations, methods of selecting antioxidants for use in such formulations, and methods of using such formulations. Oxidation or degradation due to free radicals can occur due to one or more adverse conditions, such as exposure to light, including ultraviolet, visible and/or fluorescent light, exposure to free radicals generated from other sources, and/or exposure to metal ions.

Thus, in one aspect, the invention provides aqueous pharmaceutical formulations comprising a therapeutic protein and a stabilizing amount or concentration of one, two or more antioxidants that protect the protein from oxidative degradation under one or more adverse conditions. Such formulations may optionally further comprise one or more osmolytes and/or one or more peroxide scavengers. Such formulations may also optionally further comprise other pharmaceutically acceptable diluents, excipients, carriers or adjuvants, including surfactant, salts, buffers, or preservatives at a preservative concentration. The pharmaceutical formulations may be in a ready-to-use, concentrated or lyophilized form that is reconstituted with an aqueous solution. The pharmaceutical formulations may be provided in suitable containers, kits, and/or delivery systems, including vials, ampoules, cartridges, or pre-filled syringes.

In another related aspect, the invention provides methods of preparing the formulations of the invention comprising the steps of providing a purified therapeutic protein and mixing the protein with a stabilizing amount or concentration of one, two or more antioxidants and/or one or more pharmaceutically acceptable diluents, excipients, carriers or adjuvants, and/or any of the aforementioned components such as osmolytes, peroxide scavengers, surfactant, salts, buffers or preservatives at a preservative concentration. In one embodiment, the invention provides a method of stabilizing a therapeutic protein in aqueous solution by adding a stabilizing amount or concentration of an antioxidant and a therapeutic protein to an aqueous solution, optionally further comprising the step of lyophilizing the aqueous solution. The invention provides other methods of preparing aqueous formulations of the invention comprising the step of providing a lyophilized powder or concentrated solution containing the aforementioned components and reconstituting the powder or solution with a predetermined amount of aqueous diluent, such as sterile water for injection, to produce a formulation of the invention.

In yet another aspect, the invention provides methods of using aqueous pharmaceutical formulations, involving administering the formulation to a patient to deliver the therapeutic protein at a dose that is part of a therapeutically effective dosing regimen.

A variety of pharmaceutically active proteins are contemplated for use in the formulations of the invention, including antibodies, peptibodies, erythropoiesis stimulating protein such as erythropoietin and darbepoietin, and other non-antibody proteins. In the formulations of the invention, the therapeutic protein may be present at a concentration of at least 0.1 mg/mL, and preferably is present at a therapeutically effective amount for a condition of interest.

Among the classes of antioxidant compounds contemplated for use in the formulations of the invention are cinnamic acid and derivatives thereof, or compounds of the formula (I):

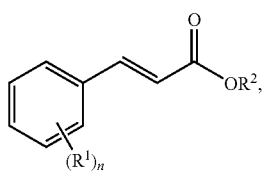

(I)

or a pharmaceutically acceptable salt or ester thereof, wherein $R^1$ is selected from the group consisting of $C_{1-8}$alkyl, hydroxy, aryl, and $OC_{1-8}$alkyl; $R^2$ is selected from the group consisting of hydrogen and $C_{1-8}$alkyl; and n is an integer from 0 to 5. Exemplary compounds of formula (I) include, but are not limited to, cinnamic acid, coumaric acid, caffeic acid, ferulic acid, sinapic acid, and chlorogenic acid. Exemplary stabilizing concentrations of antioxidants which are cinnamic acid derivatives include 0.1 mM to 20 mM.

Another class of antioxidant compounds contemplated for use in the formulations of the invention are benzoic acid and derivatives thereof, or compounds of the formula (II):

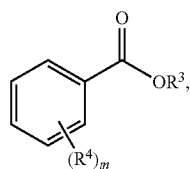

(II)

or a pharmaceutically acceptable salt or ester thereof, wherein $R^4$ is selected from the group consisting of $C_{1-8}$alkyl, hydroxy, $N(R^5)_2$, aryl, and $OC_{1-8}$alkyl; $R^3$ is selected from the group consisting of hydrogen and $C_{1-8}$alkyl; $R^5$ is independently selected from the group consisting of hydrogen and $C_{1-8}$alkyl; and m is an integer from 0 to 5, with the optional proviso that formula (II) is not benzoic acid, methyl paraben, ethyl paraben, propyl paraben, butyl paraben, benzalkonium chloride, cresol, phenol, benzyl alcohol or another known preservative. Exemplary compounds include, but are not limited to, benzoic acid, p-hydroxybenzoic acid, p-aminobenzoic acid, protocatechuic acid, gallic acid, vanillic acid, and sinapic acid. Exemplary stabilizing concentrations of antioxidants which are benzoic acid derivatives include 0.1 mM to 20 mM.

Another class of antioxidants contemplated for use in the formulations of the invention are aromatic compounds of formula (III):

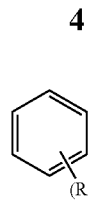

(III)

or a pharmaceutically acceptable salt or ester thereof, wherein $R^6$ is independently selected from the group consisting of $C_{1-8}$alkyl, hydroxy, $N(R^5)_2$, aryl, $OC_{1-8}$alkyl, $CO_2R^5$, $C_{2-8}$alkenyl, $C_{2-8}$alkenylCO$_2R^5$, aryl, halo, cyano, nitro, and sulfate; $R^5$ is independently selected from the group consisting of hydrogen and $C_{1-8}$alkyl; and p is an integer from 1 to 5, with the optional proviso that formula (III) is not benzoic acid, methyl paraben, ethyl paraben, propyl paraben, butyl paraben, benzalkonium chloride, cresol, phenol, benzyl alcohol, or another known preservative. Formulae (I) and (II) are encompassed in formula (III).

Where the antioxidant is a known preservative, such as benzoic acid, methyl paraben, ethyl paraben, propyl paraben, butyl paraben, m-cresol, benzyl alcohol, phenoxyethanol, benzalkonium chloride, or phenol, the antioxidant in the aqueous solution is present in a non-preservative amount. Where the formulation of the present invention contains known preservatives at a preservative concentration, it contains a different antioxidant that does not act as a preservative. Typically, when an antioxidant is used that also has preservative properties, it is used at a concentration below (e.g., at least 5%, 10%, 15%, 20% or 25% less than) its known minimum inhibitory concentration (MIC). In some specific embodiments where an antioxidant having preservative properties is used, the concentration of the antioxidant is 5 mM or less. Minimum inhibitory concentrations (MICs) are defined as the lowest concentration of an antimicrobial that will inhibit the visible growth of a microorganism after overnight incubation (Andrews, *J. Antimicrobial Chemotherapy*, 48 (Suppl. 1): 5-16 (2001)). MICs for known preservatives include the following: benzoic acid (1.6 mg/mL or 13 mM); methyl paraben (4 mg/mL or 26 mM); ethyl paraben (2 mg/mL or 12 mM); m-cresol (1.5 mg/mL or 14 mM); benzyl alcohol (5 mg/mL or 46 mM); phenoxyethanol (8.5 mg/mL or 62 mM); propyl paraben (1 mg/mL or 5.5 mM); phenol (0.6 mg/mL or 6.4 mM); butyl paraben (5 mg/mL or 26 mM); and benzalkonium chloride (0.064 mg/mL or 0.1 mM) (see Kibbe (ed.), *Handbook of Pharmaceutical Excipients*, American Pharmaceutical Association, 3rd ed. (2000)).

Other classes of antioxidant compounds (including a pharmaceutically acceptable salt or ester thereof) contemplated for use in the formulations of the invention are vitamins, such as thiamine or pyridoxine; amino acids, e.g., N-acetyl-tryptophan and proline; alpha hydroxy acids, such as glycolic acid, lactic acid, or citric acid; non-aromatic conjugated compounds, such as fumaric acid or shikimic acid; nucleobases, such as adenine, thymine, uracil, or guanine or their corresponding nucleosides, nucleotides or deoxynucleotides; flavonols or other phytochemicals found in fruits or vegetables, such as catechin, epicatehin, or furaneol; or antioxidants used in other UV protecting technologies (e.g., sunscreens) such as sulisobenzone.

Osmolytes that may be included in the formulations of the invention include amino acids, polyols, other sugars, and polyamines. Exemplary osmolytes include glycerol, sorbitol, proline, and sucrose.

Exemplary peroxide scavengers that may be included in the formulations of the invention include methionine, N-acetylcysteine, ascorbic acid, or pyruvic acid. Benzoic acid derivatives or other antioxidants may also be peroxide scavengers in addition to having photostabilizing activity.

In exemplary embodiments of the invention, the amount of the antioxidant which is added to the protein formulation ranges from about 0.0001 mM, or 0.001 mM, or 0.01 mM, to about 100 mM, or up to about 200 mM, or up to about 300 mM. In other exemplary embodiments of the invention, the ratio of protein (mg/mL) to antioxidant (mM) ranges from 1:20 to about 1:0.1, or from 200:0.001 to about 100:0.01. Other ranges contemplated include 200:0.01 to 200:1, 200: 0.1 to about 1:1, 100:1 to about 1:10, and 10:1 to about 1:20.

In a further aspect, the invention provides methods of selecting antioxidants that stabilize proteins against free radical-induced oxidation, comprising the steps of providing at least two different candidate formulations, each containing the same concentration of therapeutic protein but a different concentration of antioxidant, exposing the candidate formulations to a source that generates free radicals for a period of time, and determining biological activity or aggregation or discoloration or oxidation of the therapeutic protein within the candidate formulations. Sources that generate free radicals include ultraviolet light, visible light, fluorescent light, artificial daylight (or combinations of various types of light), peroxide, metal ions, contaminants in excipients, leachables from adhesives or plastics used in syringes and other medical devices or containers.

DETAILED DESCRIPTION OF THE INVENTION

Figure 1:
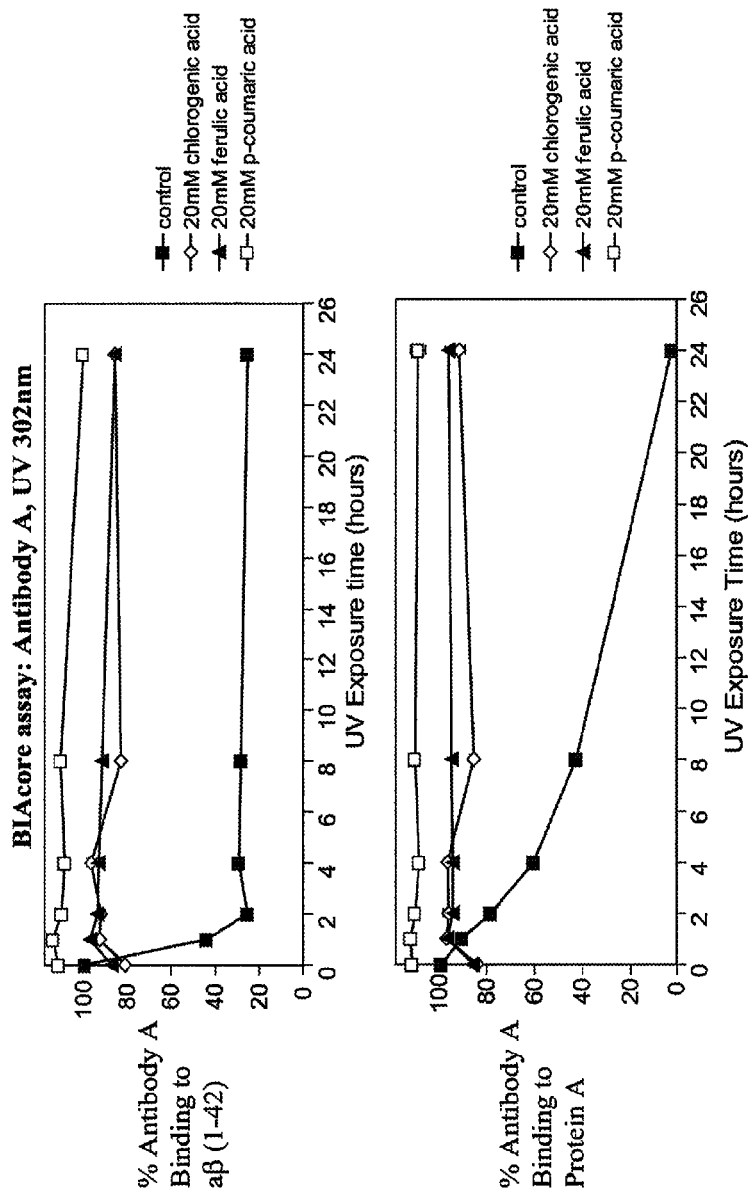
FIG. 1 shows binding of Antibody A, an IgG1 antibody, to its target antigen (top) or protein A (bottom) in formulations containing no antioxidant or 20 mM chlorogenic acid, ferulic acid, or coumaric acid, after exposure to 0-24 hours UV radiation.

Pharmaceutical formulations of therapeutic protein suitable for parenteral administration are preferably of high purity and highly stable under a variety of storage and handling conditions. The addition of antioxidants to an aqueous formulation suitable for parenteral administration has been discovered to mitigate degradation and/or oxidation of therapeutic proteins arising from UV radiation and/or free radicals, thereby expanding the range of permissible storage and handling conditions and in many cases removing the need for special packaging to avoid exposure to light, metal ions, or other sources generating free radicals. This reduction in the degradation and/or oxidation of therapeutic proteins may be demonstrated as a reduction in undesirable changes to the protein, such as protein oxidation, discoloration, protein aggregation, loss of biological activity, loss of protein tertiary structure (e.g. change in conformation, or unfolding), or other protein degradation. The improved stability imparted by inclusion of antioxidants in formulations of the invention may be exhibited under a specific set of conditions or over a wide range of conditions, including temperature, and over a substantial period of time.

As used herein, "pharmaceutical formulation" is a composition of a pharmaceutically active drug, such as a biologically active protein, that is suitable for parenteral administration to a patient in need thereof and includes only pharmaceutically acceptable excipients, diluents, carriers and adjuvants that are safe for parenteral administration to humans at the concentrations used, under the same or similar standards as for excipients, diluents, carriers and adjuvants deemed safe by the Federal Drug Administration or other foreign national authorities. A pharmaceutical formulation may be in a ready-to-use solution form, concentrated form, or a lyophilized preparation that may be reconstituted with a directed amount of diluent suitable for parenteral injection such as water, salt solution, or buffer solution.

As used herein, "parenteral" administration of a medicament or formulation means administration to a subject by a route other than topical or oral (i.e., a non-topical and non-oral route). Examples of parenteral routes include subcutaneous, intramuscular, intravascular (including intraarterial or intravenous), intraperitoneal, intraorbital, retrobulbar, peribulbar, intranasal, intrapulmonary, intrathecal, intraventricular, intraspinal, intracisternal, intracapsular, intrasternal or intralesional administration. Parenteral administration may be, e.g., by bolus injection or continuous infusion, either constant or intermittent and/or pulsatile, and may be via a needle or via a catheter or other tubing.

The present invention is directed toward aqueous pharmaceutical formulations of pharmaceutically active proteins and antioxidants that exhibit superior stability and/or resistance to oxidation or degradation induced by free radicals, methods of preparing such formulations, methods of selecting antioxidants for use in such formulations, and methods of using such formulations. Oxidation or degradation due to free radicals can occur due to one or more adverse conditions, such as exposure to light, including ultraviolet, visible and/or fluorescent light, exposure to free radicals from other sources, such as hydrogen peroxide or superoxide anions, and/or exposure to metal ions or extractables or leachables from containers.

A stable aqueous pharmaceutical formulation for parenteral administration ideally remains within its physical, chemical, microbiological, therapeutic and toxicological specifications throughout its shelf life. For example, it may retain its original clarity, color and/or odor throughout its shelf life, optionally over a relatively wide temperature range such as about 4° C. to about 37° C. or about 4° C. to about 25° C. Ideally, solutions of active pharmaceutical ingredients must be able to handle cycling temperature conditions and a range of exposure to ambient light, including UV radiation.

As used herein, the term "stabilizing concentration of antioxidant" means a concentration of antioxidant that increases the stability of a protein in a formulation compared to the stability of protein when the antioxidant is absent from the formulation, as determined under the same conditions. One example of stabilizing concentration of antioxidant is a concentration of antioxidant that reduces the degradation of the protein in the formulation compared to the degradation of the protein when calculated under the same conditions.

Preferably the stabilizing concentration of the antioxidant results in a shelf life at 2-8° C. (refrigerator temperature) of at least two months, or at least 3, 6, 9, 12, 18 or 24 months when exposed to normal ambient or fluorescent light conditions. In some embodiments, the stabilizing effect also results in a longer shelf life at other temperatures, such as 25-30° C. (room temperature). Stability of a formulation can be assessed by exposing the formulation to extreme conditions including lengthy exposure to UV-B radiation. While direct exposure to UV-B radiation is unlikely to be encountered during storage, handling, and administration of a protein therapeutic, some UV-B radiation is often present and would lead to undesirable degradation of the protein. The stabilizing effect of antioxidants in an aqueous formulation is assessed by exposing the formulations to UVB and/or other light sources including fluorescent room lighting, artificial daylight, and near UV light.

As used herein, "shelf life" means the storage period during which an active ingredient such as a therapeutic protein in a pharmaceutical formulation has minimal degradation (e.g., not more than about 10%, 9%, 8%, 7%, 6%, 5%, 4%, 3%, 2%, or 1% degradation) and/or minimal reduction in biological activity (e.g., less than 10% or less than 20%) when the pharmaceutical formulation is stored under specified storage conditions, for example, 2-8° C. and exposure to a specified light source. The amount of degradation (% degradation) can be easily determined by one of skill in the relevant art. Techniques for assessing degradation vary depending upon the identity of the protein in the pharmaceutical formulation. Exemplary techniques include size-exclusion chromatography (SEC)—HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. Exemplary pharmaceutical formulations of the present invention may exhibit degradation (e.g., fragmentation, aggregation, oxidation, or unfolding) of not more than about 2 to about 3% over 24 months when exposed to any incident light encountered during shipping, handling, or administration of the drug and stored at 2-8° C.

In exemplary embodiments, the aqueous pharmaceutical formulation of the therapeutic protein in the presence of the antioxidant retains at least 25% or at least 50%, 60%, 70%, 75%, 80%, 85%, 90%, 95%, 96%, 97%, 98% or 99% or more of its therapeutic efficacy upon exposure to conditions designed to increase free radical generation, compared to therapeutic efficacy of the same formulation when not subjected to such conditions. In other embodiments, the aqueous pharmaceutical formulation of the therapeutic protein exhibits a 50% or more improvement in stability in the presence of the antioxidant compared to its stability in the absence of antioxidant (under the same conditions), when exposed to one or more of such conditions designed to increase free radical generation. Assessment of photostability or stability upon exposure to other sources generating free radicals is described in further detail below.

The invention provides aqueous pharmaceutical formulations comprising a therapeutic protein and a stabilizing amount or concentration of one, two or more antioxidants that protect the protein from oxidative degradation under one or more adverse conditions. Where multiple antioxidants are used in combination, the required stabilizing amount or concentration of each antioxidant may be less, as part of the combination, than if the antioxidant were used alone. Exemplary classes of antioxidants are described in further detail below. Such formulations may optionally further comprise one or more osmolytes and/or one or more peroxide scavengers, described in further detail below. Such formulations may also optionally further comprise other pharmaceutically acceptable diluents, excipients, carriers or adjuvants, including surfactant, salts, or buffers, or preservatives at a preservative concentration. Where the formulation contains known preservatives at a preservative concentration, it also contains a different antioxidant that does not act as a preservative.

As used herein, a "preservative" is an agent that kills or inhibits growth of microbes, including bacteria or yeast/fungi or other microorganisms. A preservative is generally present at a "preservative concentration" that retards bacterial growth or contamination of drug products. A "non-preservative concentration" is a concentration less than the concentration that effectively prevents microbial or bacterial growth. Typically, when an antioxidant is used that also has preservative properties, it is used at a concentration below (e.g., at least 5%, 10%, 15%, 20% or 25% less than) its known minimum inhibitory concentration (MIC). For exemplary embodiments where the antioxidant also has preservative properties, the stabilizing concentration of the antioxidant may be 5 mM or less, or about 0.1 mM to about 5 mM.

In another related aspect, the invention provides methods of preparing the formulations of the invention comprising the steps of providing a purified therapeutic protein and mixing the protein with a stabilizing amount or concentration of one, two or more antioxidants. Additional steps may include mixing one or more pharmaceutically acceptable diluents, excipients, carriers or adjuvants with the protein, and optional further steps include mixing with other components such as osmolytes, peroxide scavengers, surfactant, salts, buffers or preservatives at a preservative concentration.

In one embodiment, the invention provides a method of stabilizing a therapeutic protein in aqueous solution comprising the step of adding a therapeutic protein and stabilizing amount or concentration of an antioxidant to an aqueous solution, optionally further comprising the step of lyophilizing the aqueous solution. The invention provides other methods of preparing such formulations comprising the step of providing a lyophilized powder or concentrated solution containing the aforementioned components and reconstituting the powder or solution with a predetermined amount of aqueous solution, such as sterile water for injection, to produce a formulation of the invention.

Also described in further detail below are methods of selecting desirable antioxidants for use in formulations of the invention and optimal concentrations thereof.

Therapeutic Proteins

The terms "polypeptide" and "protein" are used interchangeably herein.

The invention herein disclosed may be practiced with a variety of proteins as herein described. Among exemplary proteins in this regard are pharmaceutical proteins for veterinary and/or human therapeutic use, particularly proteins for human therapeutic use. Also among exemplary proteins are proteins that are soluble in aqueous solutions, particularly those that are soluble at relatively high concentrations and those that are stable for long periods of time.

Among the variety of pharmaceutically active proteins contemplated for use in the formulations and methods of the invention are antibodies, peptibodies, immunoglobulin-like proteins, non-antibody proteins, non-immunoglobulin-like proteins, fusion proteins such as peptibodies, Fc-fusion proteins, avimers, chimeric proteins, and/or multi-chain proteins, whether naturally occurring or non-naturally occurring. Nonlimiting examples include structural proteins, enzymes, hormones, hematopoietic factors, growth factors, cytokines, chemokines, antiobesity factors, trophic factors, anti-inflammatory factors and regulatory proteins, including but not limited to stem cell factor, leptin, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferon (alpha, beta, gamma), interleukin (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factor such as osteoprotegerin (OPG), insulin-like growth factor (IGF), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factor (CSF), bone morphogenetic protein (BMP), superoxide dismutase (SOD), tissue plasminogen activator (TPA), urokinase, streptokinase, or kallikrein. Analogs of naturally occurring proteins are contemplated for use in formulations and methods of the present invention, including polypeptides with modified glycosylation, or polypeptides without glycosylation (unglycosylated), and polypeptides with other post-translational modifications which may be made by cellular modification systems or via enzymatic and/or chemical methods.

In some embodiments, the therapeutic protein is an erythropoiesis stimulating protein. As used herein, "erythropoiesis stimulating protein" means a protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; US 2006/0111279.

As used herein, the term "analogs", when used with reference to polypeptides, refers to an amino acid sequence that has insertions, deletions or substitutions relative to the parent sequence, while still substantially maintaining the biological activity of the parent sequence, as determined using biological assays known to one of skill in the art. The formulations and methods of the invention may also include "derivatives" of naturally occurring or analog polypeptides which have been chemically modified, for example, to attach water soluble polymers (e.g., pegylated), labels (e.g., radionuclides or various enzymes), or other diagnostic or targeting or therapeutic moieties, or by insertion or substitution of non-natural amino acids by chemical means. Such derivatives will retain the binding properties of underivatized molecules of the invention.

Such polypeptides may be derived from a natural source, constructed by chemical de novo synthesis, or semi-synthesis, or recombinantly expressed, e.g., by expression of an exogenous expression construct, by activation of an endogenous gene (by homologous or non-homologous recombination, for instance), by expression of an exogenous gene under the control of an endogenous transcription control region, or any other techniques known in the art.

Further among exemplary proteins for use in the compositions and methods of the invention are proteins for pharmaceutical formulations that do not induce a highly deleterious antigenic response following administration to a subject. Exemplary in this regard are proteins for veterinary and/or human medical use, particularly, regarding the latter, humanized and human proteins.

Further among exemplary proteins of the invention are proteins that bind selectively to specific targets, including ligand-binding proteins and protein ligands. Antigen-binding proteins, proteins derived therefrom, and proteins related thereto are among the particularly exemplary embodiments of the invention in this regard.

Antibodies

Among particularly exemplary proteins that can be used in the compositions and methods of the present invention are antibody polypeptides. As used herein, the term "antibody" includes heavy or light chains, fully assembled antibodies, heavy, monoclonal antibodies (including human, humanized or chimeric antibodies), polyclonal antibodies, multispecific antibodies (e.g., bispecific antibodies), antibody fragments that can bind antigen (e.g., Fab', F'(ab)$_2$, Fv, single chain antibodies, diabodies), and polypeptides comprising 1, 2, 3, 4, 5 or all 6 complementarity determining regions (CDRs) of the foregoing, and fusion proteins or variants or derivatives thereof, as long as they exhibit the desired binding or biological activity. Antibodies of any isotype class or subclass, including IgG, IgM, IgD, IgA, and IgE, IgG1, IgG2, IgG3, IgG4, IgA1 and IgA2, or any allotype, may be used in the compositions or methods of the present invention. Antibodies may be made by any techniques known in the art, including hybridoma technologies, by activation of an endogenous gene (by homologous or non-homologous recombination, for instance), by expression of an exogenous gene under the control of an endogenous transcription control region, by expression of an exogenous expression construct, by semi-synthesis and by de novo synthesis.

The term "monoclonal antibody" as used herein refers to an antibody obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, chimeric, humanized, or human antibodies, or variants or derivatives thereof. Humanizing or modifying antibody sequence to be more human-like is described in, e.g., Jones et al., Nature 321:522 525 (1986); Morrison et al., Proc. Natl. Acad. Sci., U.S.A., 81:6851 6855 (1984); Morrison and 01, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. patent application publication nos. 20030194404, 20030031667 or 20020199213; each incorporated herein by reference.

Antibody fragments may be produced by recombinant DNA techniques or by enzymatic or chemical cleavage of intact antibodies. "Antibody fragments" comprise a portion of an intact full length antibody, preferably the antigen binding or variable region of the intact antibody, and include multispecific (bispecific, trispecific, etc.) antibodies formed from antibody fragments. Nonlimiting examples of antibody fragments include Fab, Fab', F(ab')$_2$, Fv (variable region), domain antibodies (dAb, containing a VH domain; Ward et al., Nature 341:544-546, 1989), complementarity determining region (CDR) fragments, single-chain antibodies (scFv, containing VH and VL domains on a single polypeptide chain; Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain; EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge; Olafsen, et al., Protein Eng Des Sel. 2004 April; 17(4):315-23), linear antibodies (tandem Fd segments (VH-CH1-VH-CH1; Zapata et al., Protein Eng., 8(10):1057-1062 (1995)); chelating recombinant antibodies (crAb, which can bind to two adjacent epitopes on the same antigen; Neri et al., J Mol. Biol. 246:367-73, 1995), bibodies (bispecific Fab-scFv) or tribodies (trispecific Fab-(scFv)(2); Schoonjans et al., J. Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain the antibody intracellularly (Mhashilkar et al, EMBO J. 14:1542-51, 1995; Wheeler et al., FASEB J. 17:1733-5, 2003), transbodies (cell-permeable antibodies containing a protein transduction domain (PTD) fused to scFv; Heng et al., Med. Hypotheses. 64:1105-8, 2005) nanobodies (approximately 15 kDa variable domain of the heavy chain; Cortez-Retamozo et al., Cancer Research 64:2853-57, 2004, small modular immunopharmaceuticals (SMIPs; WO 03/041600, U.S. Patent publication 2003/0133939 and US Patent Publication 2003/0118592), an antigen-binding-domain immunoglobulin fusion protein, a camelized antibody (in which VH recombines with a constant region that contains hinge, CH1, CH2 and CH3 domains; Desmyter et al., J. Biol. Chem. 276:26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "hypervariable" region or "complementarity determining region" (CDR) refers to residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991); or an alternative definition of CDR residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain). "Framework" residues are those variable region residues other than the hypervariable region residues.

The term "variant" when used in connection with antibodies refers to polypeptide sequence of an antibody that contains at least one amino acid substitution, deletion, or insertion in the variable region or the portion equivalent to the variable region, provided that the variant retains the desired binding affinity or biological activity. In addition, the antibodies of the invention may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9): 6591-6604 (2001), incorporated by reference herein in its entirety.

The term "derivative" when used in connection with antibodies refers to antibodies covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention. Conjugation of cancer-targeting antibodies to cytotoxic agent, for example, radioactive isotopes (e.g., 1131, 1125, Y90 and Re186), chemotherapeutic agents, or toxins, may enhance destruction of cancerous cells.

Methods for making bispecific or other multispecific antibodies are known in the art and include chemical cross-linking, use of leucine zippers (Kostelny et al., J. Immunol. 148:1547-1553, 1992)]; diabody technology (Hollinger et al., Proc. Natl. Acad. Sci. USA 90:6444-48, 1993); scFv dimers (Gruber et al., J. Immunol. 152: 5368, 1994), linear antibodies (Zapata et al., Protein Eng. 8:1057-62, 1995); and chelating recombinant antibodies (Neri et al., J Mol. Biol. 246:367-73, 1995).

Target Binding Proteins

Also among exemplary proteins of the invention in this regard are other types of target binding proteins, and proteins relating thereto or derived therefrom, and protein ligands, and proteins derived therefrom or relating thereto, particularly those comprising an Fc region of an antibody or a variant or derivative of an Fc region. Among exemplary ligand-binding proteins in this regard are proteins that bind signal and effector proteins, and proteins relating thereto or derived therefrom.

Peptibodies, molecules comprising an antibody Fc domain attached to at least one antigen-binding peptide, are generally described in PCT publication WO 00/24782, published May 4, 2000. Immunoglobulin-like proteins, members of the immunoglobulin superfamily, contain one or more immunoglobulin-like domains which fold in structures similar to portions of the antibody variable region.

Also contemplated with respect to the compositions and methods of the invention are formulations containing protein scaffolds that may comprise a single protein chain or a multi-polypeptide complex. Exemplary protein scaffolds are avimers, which are avidity multimers that contain a single protein chain made up of multiple domains, each of which represents a separate function (Silverman et al., Nat Biotech 23(12): 1556-1561 (2005); U.S. Patent Publication No. US 2005/0089932 A1; each of which is incorporated by reference herein in its entirety). Other protein scaffolds are reviewed in Razeghifard et al., Current Protein & Peptide Science. 8(1): 3-18, 2007, incorporated by reference herein in its entirety. Other protein scaffolds suitable for displaying peptides are reviewed in Hosse et al., Protein Science 15:14-27, 2006 (reviewing scaffolds such as the fibronectin type III domain, a lipocalin, a knottin, cytochrome b562, a kunitz-type protease inhibitor, the Z-domain, and the carbohydrate binding module CBM4-2), incorporated by reference herein in its entirety. See also Gill et al., Current Opin. Biotechnol., 17:653-658 (2006) (single domain antibodies, small modular immunopharmaceuticals, tetranectins, Adnectins, A-domain proteins, lipocalins, ankylin repeat proteins), and Skerra, J. Mol. Recognit., 13:167-187 (2000) (single domains of antibodies or of immunoglobulin superfamily, protease inhibitors, helix bundle proteins, disulfide-knotted peptides, and lipocalins), each of which is incorporated by reference herein in its entirety.

Target binding proteins, including antibodies, peptibodies, Fc fusion proteins, avimers and other protein scaffolds, and analogs or variants or derivatives thereof, that can be used in the compositions and methods of the present invention include those that bind to one or more of the following, alone or in any combination:

(i) CD proteins including but not limited to CD3, CD4, CD8, CD19, CD20, CD22, CD30, and CD34; including those that interfere with receptor binding.

(ii) HER receptor family proteins, including, for instance, HER2, HER3, HER4, and the EGF receptor;

(iii) cell adhesion molecules, for example, LFA-1, Mol, p 150,95, VLA-4, ICAM-1, VCAM, and alpha v/beta 3 integrin;

(iv) growth factors, including but not limited to, for example, vascular endothelial growth factor ("VEGF"), growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-alpha and TGF-beta, including TGF-beta1, TGF-beta2, TGF-beta3, TGF-beta4, or TGF-beta5, insulin-like growth factors -I and -II (IGF-I and IGF-II), des(1-3)-IGF-I (brain IGF-I), and osteoinductive factors;

(v) insulins and insulin-related proteins, including but not limited to insulin, insulin A-chain, insulin B-chain, proinsulin, and insulin-like growth factor binding proteins;

(vi) coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin;

(vii) other blood and serum proteins, including but not limited to albumin, IgE, and blood group antigens;

(viii) colony stimulating factors (CSFs) and receptors thereof, including the following, among others, M-CSF, GM-CSF, and G-CSF, and receptors thereof, such as CSF-1 receptor (c-fms);

(ix) receptors and receptor-associated proteins, including, for example, flk2/flt3 receptor, obesity (OB) receptor, growth hormone receptors, thrombopoietin receptors ("TPO-R," "c-mpl"), glucagon receptors, interleukin receptors, interferon receptors, T-cell receptors, stem cell factor receptors (scfr's), such as c-Kit, and other receptors listed herein;

(x) receptor ligands, including, for example, OX40L, the ligand for the OX40 receptor expressed on T cells, and other ligands listed herein;

(xi) neurotrophic factors, including but not limited to, bone-derived neurotrophic factor (BDNF) and neurotrophin-3, -4, -5, or -6 (NT-3, NT-4, NT-5, or NT-6);

(xii) relaxin A-chain, relaxin B-chain, and prorelaxin;

(xiii) interferons and interferon receptors, including for example, interferon-alpha, -beta, and -gamma, and interferon-alpha, -beta, and -gamma receptors;

(xiv) interleukins (ILs) and interleukin receptors, including but not limited to IL-1 to IL-15 and IL-1 to IL-15 receptors, such as the IL-8 receptor, among others;

(xv) viral antigens, including but not limited to, an AIDS envelope viral antigen;

(xvi) lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, DNAse, inhibin, and activin;

(xvii) integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antibodies;

(xviii) myostatins, TALL proteins, including TALL-1, amyloid proteins, including but not limited to amyloid-beta proteins, thymic stromal lymphopoietins ("TSLP"), RANK ligand ("OPGL"), c-kit, TNF receptors, including TNF Receptor Type 1, TRAIL-R2, angiopoietins, and (xix) biologically active fragments or analogs or variants of any of the foregoing.

As to all of the foregoing, particularly exemplary are those that are effective therapeutic agents, particularly those that exert a therapeutic effect by binding a target, particularly a target among those listed above, including targets derived therefrom, targets related thereto, and modifications thereof.

Particular Illustrative Proteins

Exemplary therapeutic polypeptides suitable for use in the formulations and methods of the invention include human erythropoietin (SEQ ID NO: 1) or biologically active variants, derivatives, or analogs thereof, including chemically modified derivatives. One exemplary protein is darbepoetin (SEQ ID NO: 2). Darbepoetin is a hyperglycosylated erythropoietin analog having five changes in the amino acid sequence of recombinant human EPO which provide for two additional N-linked carbohydrate chains at amino acid residues 30 and 88. The five changes in the amino acid sequence of recombinant human EPO found within the amino acid sequence of darbepoetin are Ala30Asn, His32Thr, Pro87Val, Trp88Asn, and Pro90Thr (according to the amino acid position numbering of EPO (SEQ ID NO: 1); Egrie et al., British J Cancer 84(Supplement 1): 3-10 (2001)).

Figure 2:
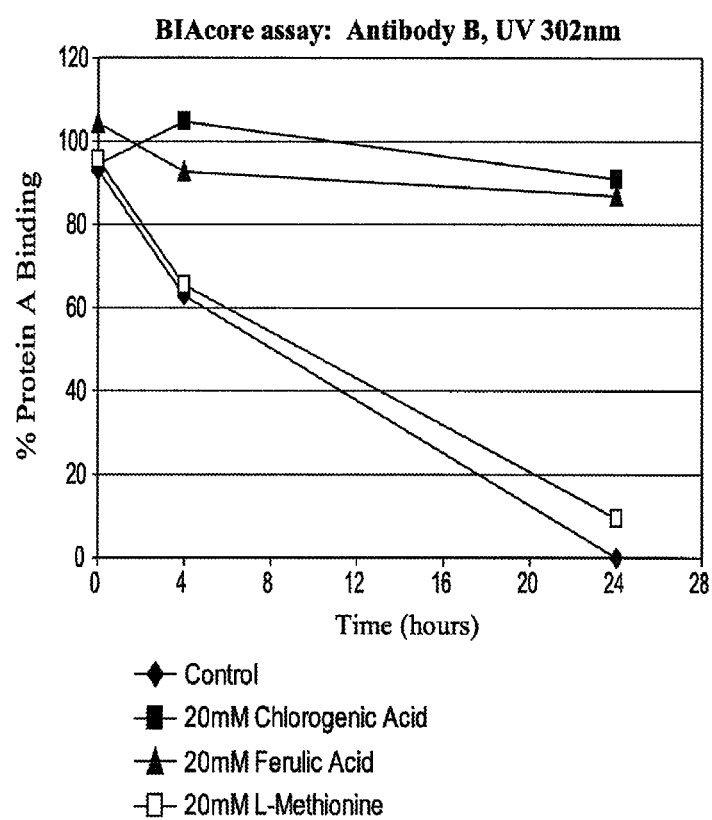
FIG. 2 shows binding of Antibody B, an IgG1 antibody, to protein A in formulations containing no antioxidant, or 20 mM chlorogenic acid, ferulic acid, or methionine, after exposure to 0-24 hours UV radiation.
Figure 4:
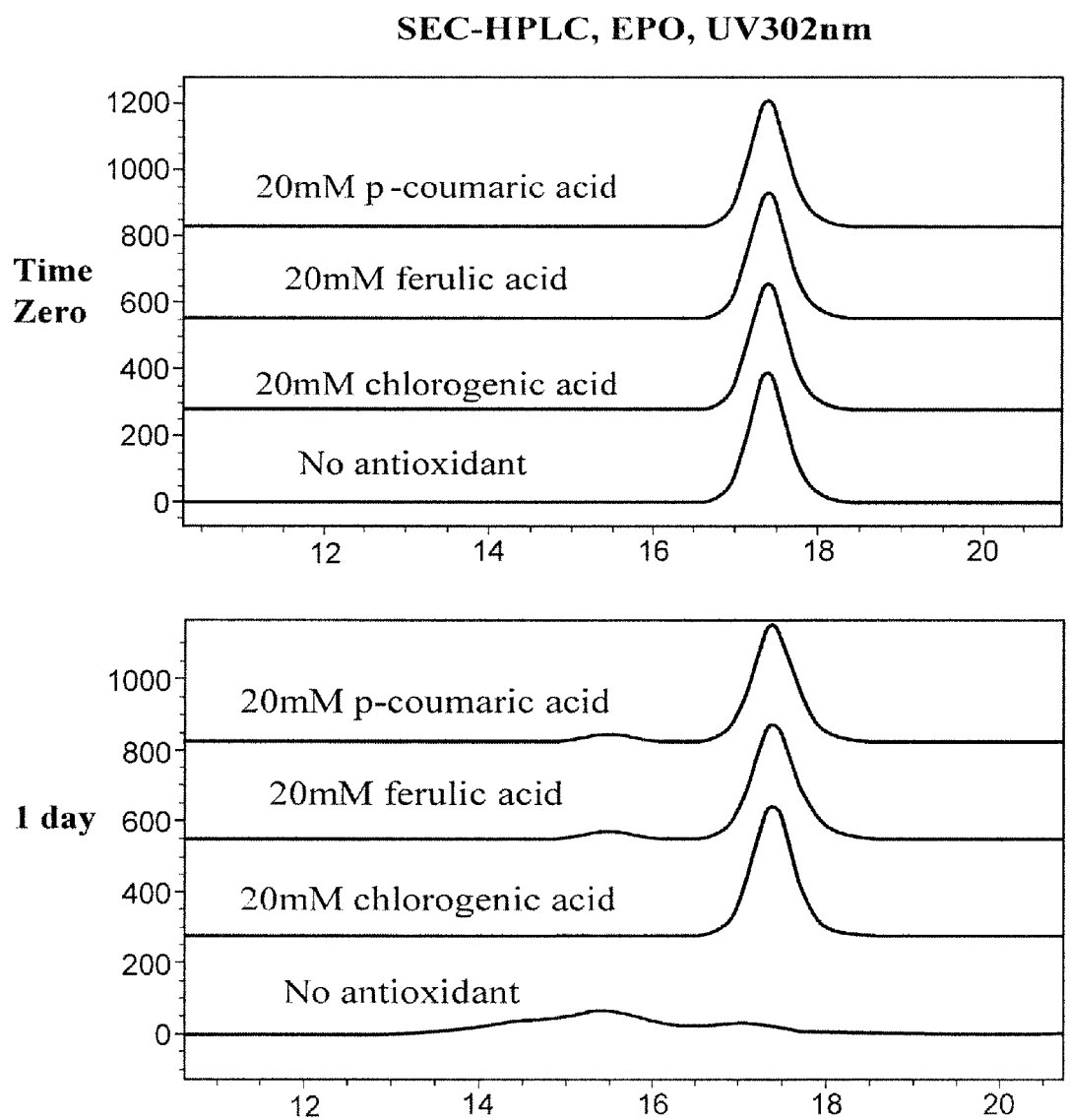
FIG. 4 shows degradation of EPO in formulations containing no antioxidant or 20 mM chlorogenic acid, ferulic acid, or coumaric acid, after exposure to 24 hours UV radiation.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in International Publication Number WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication.

Myostatin binding proteins, peptibodies, and related proteins, and the like, including myostatin specific peptibodies, particularly those described in US Application Publication Number 2004/0181033 and International Publication Number WO 2004/058988 which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication.

IL-4 receptor specific antibodies, peptibodies, and related proteins, and the like, particularly those that inhibit activities mediated by binding of IL-4 and/or IL-13 to the receptor, including those described in International Publication No. WO 2005/047331 of International Application Number PCT/US2004/03742 and in US patent application publication number 2005/112694, which are incorporated herein by reference in there entirety particularly in parts pertinent to IL-4 receptor specific antibodies, particularly such antibodies as are described therein, particularly, and without limitation, those designated therein: L1H1;

L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication.

Interleukin 1-receptor 1 ("IL1-R1") specific antibodies, peptibodies, and related proteins, and the like, including but not limited to those described in U.S. Application Publication Number US2004/097712A1 which is incorporated herein by reference in its entirety in parts pertinent to IL1—R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. application publication.

Ang2 specific antibodies, peptibodies, and related proteins, and the like, including but not limited to those described in International Publication Number WO 03/057134 and U.S. Application Publication Number US2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C$_1$K; 2xL1C; Con4C; Con4C$_1$K; 2xCon4C$_1$K; Con4-L1 (N); Con4-L1C; TN-12-9 (N); C17 (N); TN8-8(N); TN8-14 (N); Con 1 (N), also including anti-Ang 2 antibodies and formulations such as those described in International Publication Number WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication.

NGF specific antibodies, peptibodies, and related proteins, and the like including, in particular, but not limited to those described in US Application Publication Number US2005/0074821 and U.S. Pat. No. 6,919,426 which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

CD22 specific antibodies, peptibodies, and related proteins, and the like, such as those described in U.S. Pat. No. 5,789,554 which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0.

IGF-1 receptor specific antibodies, peptibodies, and related proteins, and the like, such as those described in International Patent Application Number PCT/US2005/046493, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Application.

Also among non-limiting examples of anti-IGF-1R antibodies for use in the methods and compositions of the present invention are each and all of those described in:

US Pat. App. Pub. No. 06/0040358 (published Feb. 23, 2006), 05/0008642 (published Jan. 13, 2005), 04/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

PCT Pub. No. WO 06/138729 (published Dec. 28, 2006), WO 05/016970 (published Feb. 24, 2005), and Lu et al., 2004, J Biol. Chem. 279:2856-65, including but not limited to antibodies 2F8, A12, and IMC-A12 as described therein;

PCT Pub. No. WO 07/012,614 (published Feb. 1, 2007), WO 07/000,328 (published Jan. 4, 2007), WO 06/013472 (published Feb. 9, 2006), and 05/058967 (published Jun. 30, 2005), 03/059951 (published Jul. 24, 2003);

US Pat. App. Pub. No. 05/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

US pat. App. Pub. No. 05/0249728 (published Nov. 10, 2005), 05/0186203 (published Aug. 25, 2005), 04/0265307 (published Dec. 30, 2004), 03/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

U.S. Pat. No. 7,037,498 (issued May 2, 2006), US pat. App. No. 05/0244408 (published Nov. 30, 2005), 04/0086503 (published May 6, 2004), Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

US pat. App. No. 05/0136063 (published Jun. 23, 2005), 04/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein;

US pat. App. No. 04/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors.

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Provisional Application No. 60/700,265, filed 18 Jul. 2005 and International Publication Number WO07/011,941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Provisional Application.

IL-15 specific antibodies, peptibodies, and related proteins, and the like, such as, in particular, humanized monoclonal antibodies, particularly antibodies such as those disclosed in U.S. Application Publication Numbers: US2003/0138421; US2003/023586; US2004/0071702; and U.S. Pat. No. 7,153,507 each of which is incorporated herein by reference in its entirety as to IL-15 specific antibodies and related proteins, including peptibodies, including particularly, for instance, but not limited to, HuMax IL-15 antibodies and related proteins, such as, for instance, 146B7.

IFN gamma specific antibodies, peptibodies, and related proteins and the like, especially human IFN gamma specific antibodies, particularly fully human anti-IFN gamma antibodies, such as, for instance, those described in US Application Publication Number US 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Application Publication US 2005/0004353 and in Thakur et al., Mol. Immunol. 36:1107-1115 (1999). In addition, description of the properties of these antibodies provided in US Patent Application No. US 2005/0004353 is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in US Patent Publication No. 2005/0004353. A specific antibody contemplated is antibody 1119 as disclosed in US Patent Pub No. 2005/0004353 and having a complete heavy chain of SEQ ID NO:17 as disclosed therein and having a complete light chain of SEQ ID NO:18 as disclosed therein.

TALL-1 specific antibodies, peptibodies, and the related proteins, and the like, and other TALL specific binding proteins, such as those described in U.S. Application Publication Numbers 2003/0195156 and 2006/135431 each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Application Publication.

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH.

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R.

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Patent Application Publication Number US2005/0118643 and International Publication Number WO2005/017107, huL2G7 described in U.S. Pat. No. 7,220,410 and OA-5d5 described in U.S. Pat. No. 5,686,292, 6,468,529, and in International Publication Number WO 96/38557, each of which is incorporated herein by reference in its entirety, particularly in parts pertinent to proteins that bind HGF.

TRAIL-R2 specific antibodies, peptibodies, related proteins and the like, such as those described in U.S. Provisional Applications 60/713,433 filed 31 Aug. 2005 and 60/713,478 filed 31 Aug. 2005, each of which is herein incorporated by reference in its entirety, particularly in parts pertinent to proteins that bind TRAIL-R2.

Activin A specific antibodies, peptibodies, related proteins, and the like, including but not limited to those described in U.S. Provisional Patent Application No. 60/843,430 filed 8 Sep. 2006, which is herein incorporated by reference in its entirety, particularly in parts pertinent to proteins that bind Activin A.

TGF-beta specific antibodies, peptibodies, related proteins, and the like, including but not limited to those described in U.S. Pat. No. 6,803,453 and US Patent Application Publication Number 2007/110747, each of which is herein incorporated by reference in its entirety, particularly in parts pertinent to proteins that bind TGF-beta.

Amyloid-beta protein specific antibodies, peptibodies, related proteins, and the like, including but not limited to those described in International Publication Number WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in WO 2006/081171.

c-Kit specific antibodies, peptibodies, related proteins, and the like, including but not limited to those described in U.S. Provisional Patent Application No. 60/794,771, which is incorporated herein by reference in its entirety, particularly in parts pertinent to proteins that bind c-Kit and/or other stem cell factor receptors.

OX40L specific antibodies, peptibodies, related proteins, and the like, including but not limited to those described in U.S. patent application Ser. No. 11/068,289, which is incorporated herein by reference in its entirety, particularly in parts pertinent to proteins that bind OX40L and/or other ligands of the OX040 receptor.

Other exemplary proteins include Activase® (Alteplase, tPA); Aranesp® (Darbepoetin-alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-05 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim™, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP 1Ib/Ilia receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®- (Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-B. anthracis Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Rα mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab). BR2—Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (Ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); Adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Sequence Variation

Particularly exemplary proteins in regard to all of the foregoing and the following, include those that comprise a region that is 70% or more, 80% or more, 90% or more, 95% or more, 97% or more, 98% or more, or 99% or more identical in amino acid sequence to a reference amino acid sequence of a binding protein, as illustrated above, particularly a pharmaceutical binding protein, such as a GenBank or other reference sequence of a reference protein.

Identity in this regard can be determined using a variety of well-known and readily available amino acid sequence analysis software. Exemplary software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

The BLASTN, BLASTX, and BLASTP programs are among exemplary programs for such determinations, the former for polynucleotide sequence comparisons and the latter two for polypeptide sequence comparisons; particularly BLASTX for comparison of the polypeptide sequences from all three reading frames of polynucleotide sequence and BLASTP for a single polypeptide sequence.

BLAST provides a variety of user definable parameters that are set before implementing a comparison. Some of them are more readily apparent than others on graphical user interfaces, such as those provided by NCBI BLAST and other sequence alignment programs that can be accessed on the internet. The settings and their values are set out and explained on the service web sites and are explained and set out in particular detail in a variety of readily available texts, including but not limited to BIOINFORMATICS: SEQUENCE AND GENOME ANALYSIS, 2nd Ed., David W. Mount, Cold Spring Harbor Laboratory Press, Cold Spring Harbor, N.Y. (2004), especially Chapters 3, 4, 5, and 6 as to comparison of protein and nucleic acid sequences in general and as to BLAST comparisons and searches in particular; SEQUENCE ANALYSIS IN A NUTSHELL: A GUIDE TO COMMON TOOLS AND DATABASES, Scott Markel and Darryl Leon, O'Reilly & Associates, Sebastopol, Calif. (2003), especially Chapter 7 as to BLAST in particular, each of which is herein incorporated by reference in its entirety particularly in parts pertinent to comparison of nucleotide and polypeptide sequences and to determining their degree of identity, similarity, homology and/or the like, especially as to comparison of a test sequence and a reference sequence to calculate a degree (percent) of identity between them.

In exemplary embodiments of the invention in this regard, relatedness of sequences is defined as the identity score in percent returned by any one or another of the aforementioned BLAST comparison searches with e=10 and all other parameters set to their default values on the NCBI web server as set forth in SEQUENCE ANALYSIS IN A NUTSHELL: A GUIDE TO COMMON TOOLS AND DATABASES, Scott Markel and Darryl Leon, O'Reilly & Associates, Sebastopol, Calif. (2003), pages 47-51 which are incorporated herein by reference in their entireties and in all particulars of the exemplary settings for parameters of the present invention for comparing sequences using BLAST, such as those on NCBI BLAST.

The following references provide additional information on sequence comparisons in this regard, and in others. GUIDE TO HUMAN GENOME COMPUTING, Ed. Martin J. Bishop, Academic Press, Harcourt Brace & Company Publishers, New York (1994), which is incorporated herein by reference in its entirety with regard to the foregoing, particularly in parts pertinent to determining identity and or homology of amino acid or polynucleotide sequences, especially Chapter 7. The BLAST programs are described in Altschul et al., "Basic Local Alignment Research Tool," J Mol Biol 215: 403-410 (1990), which is incorporated by reference herein in its entirety. Additional information concerning sequence analysis and homology and identity determinations are provided in, among many other references well-known and readily available to those skilled in the art: NUCLEIC ACID AND PROTEIN SEQUENCE ANALYSIS: A PRACTICAL APPROACH, Eds. M. J. Bishop and C. J. Rawings, IRL Press, Oxford, UK (1987); PROTEIN STRUCTURE: A PRACTICAL APPROACH, Ed. T. E. Creighton, IRL Press, Oxford, UK (1989); Doolittle, R. F.: "Searching through sequence databases," Met Enz. 183: 99-110 (1990); Meyers and Miller: "Optimal alignments in linear space" Comput. Applica. in Biosci 4: 11-17 (1988); Needleman and Wunsch: "A general method applicable to the search for similarities in amino acid sequence of two proteins," J Mol Biol 48: 443-453 (1970) and Smith and Waterman "Identification of common molecular subsequences," J Mol Biol 147: 1950 et seq. (1981), each of which is incorporated herein by reference in its entirety with reference to the foregoing, particularly in parts pertinent to sequence comparison and identity and homology determinations.

Particularly exemplary embodiments in this regard have 50% to 150% of the activity of the aforementioned reference protein, particularly highly exemplary embodiments in this regard have 60% to 125% of the activity of the reference protein, yet more highly exemplary embodiments have 75% to 110% of the activity of the reference protein, still more highly exemplary embodiments have 85% to 125% the activity of the reference, still more highly exemplary embodiments have 90% to 110% of the activity of the reference.

In the formulations of the invention, the therapeutic protein may be present at a concentration of at least 0.1 mg/mL, and preferably is present at a therapeutically effective amount for a condition of interest. Exemplary protein concentrations in the formulation may range from about 1 mg/ml to about 180 mg/ml or from about 1 mg/mL to about 50 mg/mL, or from about 1 mg/mL to about 25 mg/mL, or alternatively from about 1 mg/mL to about 10 mg/mL. The concentration of protein will depend upon the end use of the aqueous formulation and can be easily determined by a person of skill in the art. Particularly contemplated concentrations of protein are at least about 1.5, 2.0, 2.5, 3.0, 3.5, 4.0, 5.0, 6.0, 7.0, 8.0, 9.0, 10.0, 15.0, 20.0, 25.0, 30.0, 35.0, or 40.0, or up to about 15.0, 20.0, 25.0, 30.0, 35.0, 40.0, 45.0, 50.0, 55.0, 60.0, 65.0, 70.0, 75.0, 80.0, 85.0, 90.0, 95.0, 100.0, 105.0, 110.0, 115.0, 120.0, 125.0, 130.0, 140.0 or 150.0 mg/mL.

Antioxidants

"Antioxidants" are electron-rich molecules that (a) contain a conjugated system of double bonds, (b) comprise at least two double bonds of the same or different types (for example, a carbon-carbon or carbon-nitrogen double bond), (c) contain no more than 3 rings (e.g., 0, 1, 2 or 3 rings), and/or (d) inhibit damage to a protein caused by free radicals. Antioxidants thus retard or prevent oxidation of a therapeutic protein in an aqueous formulation due to exposure to light, including ultraviolet, visible and/or fluorescent light, and/or exposure to free radicals generated from other sources, such as peroxides, superoxide anions, or metal ions. Antioxidants include both aromatic and conjugated molecules. Without being bound by a theory of the invention, one mechanism of action of antioxidants is believed to involve the resonance stabilization of free radicals by the conjugated system of double bonds. Absorption of UV radiation or reaction with reactive oxygen species results in abstraction of a proton from the antioxidant and the generation of a stabilized radical species. Due to the lower free energy state of this radical species compared to that involving oxygen species or protein amino acids, further reaction becomes energetically unfavorable and the radical remains trapped within the anti-oxidant. As a result, damage such as oxidation to protein by free radical can be inhibited. Phenolic compounds and any compounds containing conjugated systems of double bonds allow for resonance stabilization of radical species and are effective antioxidants.

Exemplary classes of antioxidants of the invention include cinnamic acid and derivatives thereof, or benzoic acid and derivatives thereof, exemplified by the compounds of formula (I) or (II), respectively:

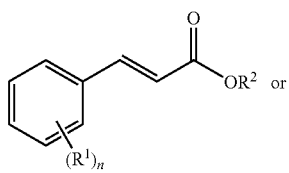

(I)

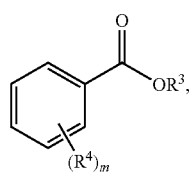

(II)

or a pharmaceutically acceptable salt or ester thereof, where $R^1$ is selected from the group consisting of $C_{1-8}$alkyl, hydroxy, aryl, and $OC_{1-8}$alkyl; $R^2$ is selected from the group consisting of hydrogen and $C_{1-8}$alkyl; and n is an integer from 0 to 5; and wherein $R^4$ is selected from the group consisting of $C_{1-8}$alkyl, hydroxy, $N(R^5)_2$, aryl, and $OC_{1-8}$alkyl; $R^3$ is selected from the group consisting of hydrogen and $C_{1-8}$alkyl; $R^5$ is independently selected from the group consisting of hydrogen and $C_{1-8}$alkyl; and m is an integer from 0 to 5. Exemplary compounds suitable as antioxidants in the formulations disclosed herein include, but are not limited to,

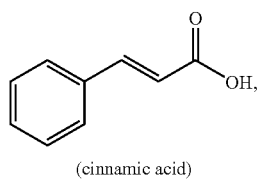
(cinnamic acid)

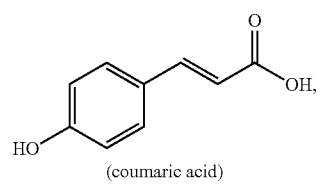
(coumaric acid)

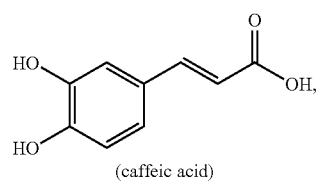
(caffeic acid)

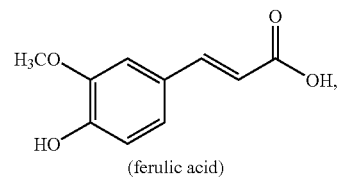
(ferulic acid)

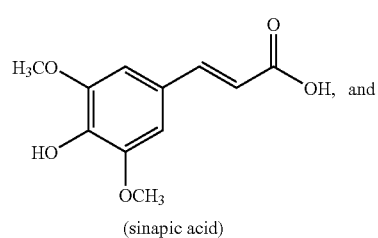
(sinapic acid)

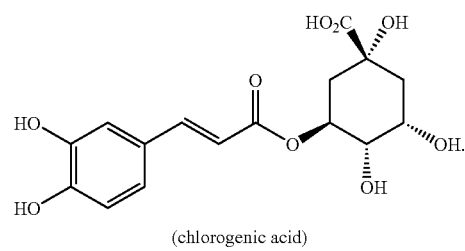
(chlorogenic acid)

Explempary compounds of formula (II) include, but are not limited to,

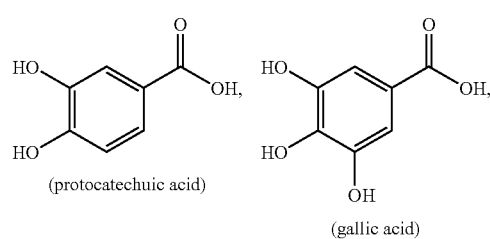
(protocatechuic acid) (gallic acid)

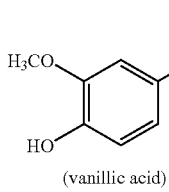

(vanillic acid)

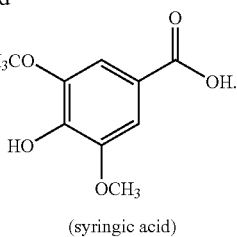

(syringic acid)

Alternatively and/or additionally, a pharmaceutically acceptable salt or ester of antioxidants disclosed herein can also be used as an antioxidant for the aqueous formulations suitable for parenteral administration disclosed herein.

Another class of antioxidants contemplated for use in the formulations of the invention are aromatic compounds of formula (III):

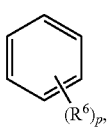

or a pharmaceutically acceptable salt or ester thereof, wherein $R^6$ is independently selected from the group consisting of $C_{1-8}$alkyl, hydroxy, $N(R^5)_2$, aryl, $OC_{1-8}$alkyl, $CO_2R^5$, $C_{2-8}$alkenyl, $C_{2-8}$alkenyl$CO_2R^5$, aryl, halo, cyano, nitro, and sulfate; $R^5$ is independently selected from the group consisting of hydrogen and $C_{1-8}$alkyl; and p is an integer from 0 to 5. Formulae (I) and (II) are encompassed in formula (III).

Optionally excluded from the scope of formulae (I), (II) and/or (III) are known preservatives such as benzoic acid, p-hydroxybenzoic acid, methyl paraben, ethyl paraben, cresol, phenol, or benzyl alcohol.

As used herein, the term "alkyl" includes straight chained and branched hydrocarbon groups containing the indicated number of carbon atoms, such as methyl, ethyl, and straight chain and branched propyl and butyl groups. The hydrocarbon group can contain up to 8 carbon atoms. The term "alkyl" also encompasses alkyl groups which are optionally substituted with, e.g., one or more halogen atoms, one or more hydroxyl groups, one or more thiol groups, or one or more carboxylic acid groups. Also encompassed by the term "alkyl" are cycloalkyl groups. "Cycloalkyl" is defined as a cyclic $C_3$-$C_8$ hydrocarbon group, e.g., cyclopropyl, cyclobutyl, cyclohexyl, and cyclopentyl. "Heterocycloalkyl" is defined similar to cycloalkyl, except at least one heteroatom is present in the cyclic structure. Suitable heteroatoms include N, S, and O. The term "alkenyl" is defined identically as "alkyl," except for containing a carbon-carbon double bond.

The term "halo" or "halogen" is defined herein to include fluorine, bromine, chlorine, and iodine.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxy, C(=O)OR, hydroxyalkyl, alkoxy, alkoxyalkyl, haloalkyl, haloalkoxy, cyano, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "hydroxy" is defined as —OH.
The term "alkoxy" is defined as —OR, wherein R is alkyl.
The term "cyano" is defined as —CN.
The term "nitro" is defined as —$NO_2$.
The term "sulfate" is defined as —$SO_3H$.

Other classes of antioxidant compounds (including a pharmaceutically acceptable salt or ester thereof) contemplated for use in the formulations of the invention are vitamins, such as thiamine or pyridoxine.

Amino acids or amino acid derivatives, e.g., N-acetyl-tryptophan and proline and alpha hydroxy acids, such as glycolic acid, lactic acid, or citric acid are also suitable antioxidants for use according to the invention.

Non-aromatic conjugated compounds, such as fumaric acid or shikimic acid, are also suitable antioxidants for use according to the invention.

Nucleobases or chemical analogs or derivatives thereof, such as cytosine, adenine, thymine, uracil, guanine or their corresponding nucleosides, nucleotides or deoxynucleotides are a suitable class of antioxidants for use according to the invention.

A large class of antioxidants includes flavonols or other phytochemicals found in fruits or vegetables, such as catechin, epicatehin, or furaneol. Other categories of phytochemicals include flavones, flavonols, flavanoids, flavanones, isoflavones, and anthocyanidins. Additional specific compounds contemplated include, but are not limited to, quercetin, epicatechin gallate, and epigallocatechin gallate.

Yet another class of antioxidants includes those used in other UV protecting technologies (e.g., suncreens) such as sulisobenzone. Other compounds contemplated in this class of antioxidants include all FDA or other national or region regulation authority approved sunscreen active ingredient, such as amniobenzoic acid, avobenzone, cinoxate, dioxybenzone, homosalate, menthyl antranilate, octocrylene, octyl methoxycinnamate, octyl salicylate, oxybenzone, padimate, phenylbenzimidazole sulfonic acid, titanium dioxide, trolamine salicylate, and zinc oxide.

In exemplary embodiments of the invention, the amount of the antioxidant which is added to the protein formulation ranges from about 0.0001 mM to about 100 mM.

The antioxidant can be present in any amount that is effective to stabilize the aqueous formulation. Typically, the concentration of the antioxidant is about 0.0001 mM to about 100 mM. Exemplary ranges for particularly effective antioxidants include about 0.0001 to about 0.005 mM, or about 0.0005 to about 0.002 mM. Other exemplary ranges include about 0.001 to about 0.01 mM, about 0.001 to about 0.1 mM, about 0.01 to about 1 mM, about 0.1 to about 25 mM, or about 0.1 to about 50 mM, or about 0.1 mM to about 100 mM. Also contemplated are concentrations of about 0.005, 0.006, 0.007, 0.008, 0.009, 0.01, 0.011, 0.012, 0.013, 0.14, 0.015, 0.016, 0.017, 0.018, 0.019, 0.02, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.04, 0.041, 0.042, 0.043, 0.044, 0.045, 0.046, 0.047, 0.048, 0.049, 0.05, 0.051, 0.052, 0.053, 0.054, 0.055, 0.056, 0.057, 0.058, 0.059, 0.06, 0.061, 0.062, 0.063, 0.064, 0.065, 0.066, 0.067, 0.068, 0.069, 0.070, 0.071, 0.072, 0.073, 0.074, 0.074, 0.075, 0.076, 0.077, 0.078, 0.079, 0.08, 0.081, 0.082, 0.083, 0.084, 0.085, 0.086, 0.087, 0.088, 0.089, 0.09, 0.091, 0.092, 0.093, 0.094, 0.095, 0.096, 0.097, 0.098, 0.099, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, and 59 mM.

In other exemplary embodiments of the invention, the ratio of protein (mg/mL) to antioxidant (mM) ranges from 1:20 to about 1:0.1. Exemplary ratios of therapeutic protein to antioxidant of aqueous formulations suitable for parenteral administration of the present invention are about 1 mg/mL therapeutic protein or antibody: 20 mM antioxidant to about 1 mg/mL protein or antibody: 0.1 mM antioxidant. Also contemplated are ratios of protein or antibody to antioxidant of about 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 1:0.9; 1:0.8; 1:0.7; 1:0.6; 1:0.5; 1:0.4; 1:0.3; and 1:0.2.

In embodiments where the antioxidant may also be a known preservative, such as, e.g., benzoic acid, benzyl alcohol, methyl or ethyl paraben, m-cresol, or phenol, the concentration of antioxidant is a non-preservative concentration. In order for preservatives to effectively guard against microbial or bacterial growth, they must be present in sufficient concentration. In some embodiments, when compounds that have been used as preservatives are part of the disclosed aqueous formulations of the present invention, they are present in amount of less than 10 mM; less than 7 mM; or, 5 mM or less. In some embodiments, when the antioxidant is a known preservative, the concentration of the antioxidant is a non-preservative concentration of 0.1 mM to 5 mM. In some specific embodiments, the antioxidant comprises benzyl alcohol, methyl paraben, ethyl paraben, m-cresol, and/or phenol and has a concentration of 0.1 mM to 5 mM.

Typically, when an antioxidant is used that also has preservative properties, it is used at a concentration below (e.g., at least 5%, 10%, 15%, 20% or 25% less than) its known minimum inhibitory concentration (MIC). Minimum inhibitory concentrations (MICs) are defined as the lowest concentration of an antimicrobial that will inhibit the visible growth of a microorganism after overnight incubation (Andrews, *J. Antimicrobial Chemotherapy*, 48(Suppl. 1): 5-16 (2001)). Minimum bactericidal concentrations (MBCs) are the lowest concentration of antimicrobial that will prevent the growth of an organism after subculture on to antibiotic-free media. MICs are used by diagnostic laboratories mainly to confirm resistance, but most often as a research tool to determine the in vitro activity of new antimicrobials, and data from such studies have been used to determine MIC breakpoints. MBC determinations are undertaken less frequently and their major use has been reserved for isolates from the blood of patients with endocarditis. Standardized methods for determining MICs and MBCs are described in Andrews, *J. Antimicrobial Chemotherapy*, 48(Suppl. 1): 5-16 (2001), which is incorporated by reference in its entirety. The method gives information on the storage of standard antibiotic powder, preparation of stock antibiotic solutions, media, preparation of inocula, incubation conditions, and reading and interpretation of results.

MIC values are specific for specific microorganisms. Thus, there are a variety of MICs for a given preservative, depending upon the microorganism being considered. However, preservatives are often added to an amount that is at a concentration of one of its higher MICs, so as to be effective against a wide variety of microorganisms. MICs for known preservatives include the following: benzoic acid (1.6 mg/mL or 13 mM); methyl paraben (4 mg/mL or 26 mM); ethyl paraben (2 mg/mL or 12 mM); m-cresol (1.5 mg/mL or 14 mM); benzyl alcohol (5 mg/mL or 46 mM); phenoxyethanol (8.5 mg/mL or 62 mM); propyl paraben (1 mg/mL or 5.5 mM); phenol (0.6 mg/mL or 6.4 mM); butyl paraben (5 mg/mL or 26 mM); and benzalkonium chloride (0.064 mg/mL or 0.1 mM) (see Kibbe (ed.), *Handbook of Pharmaceutical Excipients*, American Pharmaceutical Association, 3rd ed. (2000)).

Osmolytes

Formulations of the invention can include an osmolyte and/or a peroxide scavenger. As used herein, "osmolytes" are small, organic compounds with no net charge. These include zwitterionic compounds (compounds that contain charged species, but whose overall charge is zero due to equal numbers of positive and negative charges). Examples of osmolytes contemplated for use in the present invention include, but are not limited to, sugars (e.g., sucrose, glucose, trehalose, fructose, xylose, mannitose, fucose), polyols (e.g., glycerol, mannitol, sorbitol, glycol, inositol), amino acids, including free amino acids and derivatives thereof (e.g., glycine, proline, valine, leucine, alanine, glutamine, glycine betaine), polyamine or amine, and trimethylamino N-oxide (TMAO). Other osmolytes contemplated include choline, betaine, phosphorylcholine, glycerophosphorylcholine, creatine, creatine phosphate, glutamate, aspartate, and taurine.

Exemplary ranges of concentrations of osmolytes in an aqueous formulation suitable for parenteral administration of the present invention are between about 0.05 M to about 3.5 M, about 0.1 M to about 3.0 M, or about 0.2 M to about 2.0 M. Also contemplated are concentrations of osmolyte of about 0.35, about 0.4, about 0.45, about 0.5, about 0.55, about 0.6, about 0.65, about 0.7, about 0.75, about 0.8, about 0.85, about 0.9, about 0.95, about 1.0, about 1.05, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, and about 1.95 M.

Peroxide Scavengers

The term "peroxide scavenger" as used herein, refers to a compound capable of reacting with, to eliminate or reduce, peroxide, alkyl, alkyl peroxide, or hydrogen radicals or mixtures thereof. Exemplary peroxide scavengers that may be included in the formulations of the invention include methionine, N-acetylcysteine, ascorbic acid, pyruvic acid, or any thiol ether or thiol compound, and other such compounds. Benzoic acid and its derivatives or other antioxidants may also function as peroxide scavengers, in addition to their photo stabilizing effects.

Exemplary ranges of concentrations of peroxide scavengers include about 1 mM to about 50 mM, or about 1 mM to about 40 mM, or about 1 mM to about 30 mM. In some cases, the peroxide scavenger can be greater than 50 mM up to about 250 mM. Also contemplated are concentrations of peroxide scavengers of about 1.5, about 2, about 2.5, about 3, about 3.5, about 4, about 4.5, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 20.5, about 21, about 21.5, about 22, about 22.5, about 23, about 23.5, about 24, about 24.5, about 25, about 25.5, about 26, about 26.5, about 27, about 27.5, about 28, about 28.5, about 29, about 29.5, about 30, about 30.5, about 31, about 31.5, about 32, about 32.5, about 33, about 33.5, about 34, about 34.5, about 35, about 36, about 37, about 38, about 39, about 40, about 41, about 42, about 43, about 44, about 45, about 46, about 47, about 48, and about 49 mM.

Assessment of Stability Including Photostability

The stability of a pharmaceutical formulation to exposure to light or other sources generating free radicals can be assessed using any means and any assay conditions known in the art. Generally, a batch of a pharmaceutical formulation is prepared and stored under a specified set of conditions. The conditions may be designed to mimic normal storage conditions or alternatively may be exaggerated storage conditions designed to increase the rate of chemical or physical degradation or oxidation of the drug substance, also called accelerated testing or stress testing. Samples of each batch of formulation are then analyzed at different time points for stability. For example, under normal storage conditions, exemplary time points include time zero, 2 weeks, 1 month, 3 months, 6 months, 9 months, 1 year, 18 months and/or 2 years. Depending on the exaggerated storage conditions, exemplary time points could include assessment at time zero, 0.5 hours, 2 hours and/or 24 hours, or 1 day, 2 days, 7 days and/or 2 weeks. Studies on drug products are carried out in a sequential manner starting with testing the fully exposed product then progressing as necessary to the product in the immediate pack and then to the marketing pack.

Extreme conditions designed to greatly increase free radical generation include exposure to UVA and/or UVB light at 4° C. to 25° C. for 0.5 to 24 hours, or exposure to a 1% solution of hydrogen peroxide at 25° C. for 2 weeks, or exposure to 0.2 mM Fe-EDTA, 0.3% $H_2O_2$, and 1 mM ascorbate for 2 hours or longer at 37° C. Samples may alternatively be exposed to light providing an overall illumination of not less than 1.2 million lux hours and an integrated near UV energy of not less than 200 watt hours/square meter.

The International Conference on Harmonisation of Technical Requirements for Registration of Pharmaceuticals for Human Use (ICH) guidelines for photostability testing of a new drug substance gives recommendations for the light sources and exposure times that should be tested to ensure that such an exposure does not result in undesirable change. Two options for light sources are given by this guideline. The include (1) any light source that is designed to produce an output similar to the D65/ID65 emission standard such as an artificial daylight fluorescent lamp combining visible and ultraviolet outputs, xenon, or metal halide lamp; or (2) the sample is exposed to both a cool white fluorescent and near ultraviolet lamp. The cool white fluorescent lamp is set to produce an output similar to that specified in ISO 10977. The near UV fluorescent lamp has a spectral distribution from 320 nm to 400 nm with a maximum energy emission between 350 nm and 370 nm. A significant proportion of UV is in both bands of 320 nm to 360 nm and 360 nm to 400 nm.

The stability of a therapeutic protein in an aqueous formulation can be assessed in a variety of ways, including by measuring degradation, aggregation, activity of the therapeutic protein in comparison to a standard, discoloration, and/or protein oxidation. For comparison, the same concentration protein in two formulations in the presence and absence of antioxidant (or other components) can be monitored to determine the beneficial effect on stability and shelf-life.

Techniques for assessing degradation vary depending upon the identity of the protein in the pharmaceutical formulation. Exemplary techniques include size-exclusion chromatography (SEC)—HPLC to detect, e.g., aggregation, reverse phase (RP)—HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. Stability can be assessed in many ways, including monitoring conformational change over a range of temperatures (thermostability) and/or time periods (shelf-life) and/or after exposure to stressful handling situations (e.g. physical shaking). The amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including using differential scanning calorimetry (DSC), e.g. to determine the temperature of denaturation, or circular dichroism (CD), which measures the molar ellipticity of the protein. Fluorescence can also be used to analyze the composition. Fluorescence encompasses the release or absorption of energy in the form of light or heat, and changes in the polar properties of light. Fluorescence emission can be intrinsic to a protein or can be due to a fluorescence reporter molecule. For example, ANS is a fluorescent probe that binds to the hydrophobic pockets of partially unfolded proteins. As the concentration of unfolded protein increases, the number of hydrophobic pockets increases and subsequently the concentration of ANS that can bind increases. This increase in ANS binding can be monitored by detection of the fluorescence signal of a protein sample.

Assessing biologic activity of the therapeutic protein depends on the protein and can be measured by suitable assays readily determined by those of ordinary skill in the art. For example, for antibodies, retention of binding affinity or avidity (as measured, e.g., through BIAcore assays) to the antibody's specific target antigen are a relevant measure of biological activity. For non-antibody proteins, retention of tertiary conformation can be assessed by ability to bind to its natural ligand or its natural receptor, or by ability to bind to antibodies that recognize epitopes important for biological activity, or by suitable in vitro or in vivo biological activity tests.

Discoloration can be assessed visually or by measurement of absorbance at a specific wavelength. Protein oxidation can be assessed by peptide mapping.

One exemplary test for determining the stability of a formulation as disclosed herein is to expose the protein formulation for 3 hours to UVB light, using, for example, a 8 watt mid UV lamp having a spectral distribution from 270 nm to 360 nm with a maximum energy emission about 302 nm. Another example for determining stability of a formulation includes exposing a formulation to UV light using a near UV fluorescent lamp having a spectral distribution from 320 nm to 400 nm, with a maximum energy emission between 350 nm and 370 nm. The overall illumination of the formulation should be at least 1.2 million lux hours and an integrated near UV energy of at least 200 watt hours/m². The formulation is then subjected to SEC chromatography to determine the percent of protein remaining in the formulation. The formulations disclosed herein typically exhibit less than 10% degradation after exposure to UVB and/or UV light preferably exhibit less than 9%, less than 8%, less than 7%, less than 6%, less than 5%, less than 4%, less than 3%, less than 2%, or less than 1%.

An exemplary protocol for Met-54 oxidation and peroxide assay is as follows. 0.6% hydrogen peroxide is added to 20 mM sodium phosphate solution containing 0.336 m/mL erythropoietin (EPO). Following 24 hours incubation at room temperature, 1 µg of the enzyme catalase is added to quench the excess hydrogen peroxide. 10 µL of 1M Tris solution pH 8.0 is added to 90 µL of EPO solution followed by addition of 2 µL of a 1 mg/mL trypsin solution. Samples are incubated overnight at room temperature. Peptides are separated using reverse phase HPLC(RP-HPLC). Peptides are identified by mass spectrometry (LC-MS). % Met-54 oxidation is calculated using peak areas determined by integration of UV chromatogram from RP-HPLC Other means for measuring stability can be used and are well known to persons of skill in the art. All of these techniques can be used singly or in combination to assess the degradation of the protein in the pharmaceutical formulation and determine the stability of the aqueous formulation.

The invention also provides methods of selecting antioxidants that stabilize proteins against free radical-induced oxidation, comprising the steps of providing at least two different candidate formulations, each containing the same concentration of therapeutic protein but a different concentration of antioxidant, exposing the candidate formulations to a source that generates free radicals for a period of time, and determining biological activity or aggregation or discoloration or oxidation of the therapeutic protein within the candidate formulations. Sources that generate free radicals include ultraviolet light, visible light, fluorescent light, artificial daylight (or combinations of various types of light), peroxide, metal ions, or contaminants or leachables in excipients or in storage containers or medical devices such as syringes and the like.

The selection of an antioxidant for use in an aqueous protein formulation of the invention may involve testing candidate antioxidants for solubility, compatibility, and effectiveness. For a given protein or antibody, a formulation is selected with an optimal pH value that maximizes long-term shelf stability of the protein. The chosen pH impacts the subsequent selection of effective antioxidants for inclusion in the formulation. Antioxidants such as the cinnamic acid derivatives and benzoic acid derivatives contain an ionizable carboxylic acid group with a pKa of approximately 4.5. As a result, the solubility of these compounds decreases as the pH approaches 4.5. The pH and the presence of differing ratios of acid and base forms of the antioxidant may also affect the stabilizing activity of the antioxidant, as well as the color and appearance of the antioxidant in solution. The protein concentration, the sensitivity of the protein to oxidation, and the possibility that the protein will encounter light or other source of free radicals is considered in determining the concentration and potency of antioxidants necessary for adequate protection. In turn, adjustments may be made to the formulation pH to accommodate higher concentrations of a particular antioxidant. Antioxidants with sufficient solubility and lack of color at a given pH are tested at a range of concentrations to determine level of effectiveness as well as effect on shelf stability of the protein.

Containers and Kits

The pharmaceutical formulations may be provided in suitable containers, kits, and/or delivery systems. Exemplary containers include vials for injection, ampoules, cartridges, pre-filled syringes, or other containers known in the art. Vials may comprise a pierceable elastomeric seal for access via needle, or may comprise a special cap or valve adapted for needle-less access to the contents by a syringe or other tubing. Further disclosed herein are single-use containers comprising aqueous formulations of the invention. Aqueous formulations in single-use containers do not contain preservatives as the formulation is only used once so no microbial or bacterial growth need be guarded against. Thus, for single-use aqueous formulations of the invention, known preservatives may be specifically included in the classes of antioxidants used according to the invention.

Kits may contain one container and instructions. Kits may contain two containers, one of which contains lyophilized powder or concentrated solution and the other of which contains a desired amount of water for injection or other aqueous solution for reconstitution of the lyophilized powder.

Delivery systems include implantable depots containing drug formulation, cartridges, syringes, infusion pumps, or other delivery systems known in the art.

The invention also provides methods of using aqueous pharmaceutical formulations, involving administering the formulation to a patient to deliver the therapeutic protein at a dose that is part of a therapeutically effective dosing regimen.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The examples described herein were prepared and studied for their stability. Samples of different therapeutic proteins were made—recombinant human-erythropoietin (EPO) (SEQ ID NO: 1), Antibody A (an IgG1 monoclonal antibody), Antibody B (another IgG1 monoclonal antibody, which binds specifically to human interferon γ), and antistreptavidin (a IgG2 monoclonal antibody)—with different antioxidants and with no antioxidant as a control.

For the examples below involving exposure to UVB radiation, each sample was exposed to UVB light ($\lambda \approx 302$ nm) for varying times, using a UVP 8W modle UVLMS-38 lamp at 4° C. The formulations were then analyzed using size exclusion chromatography high pressure liquid chromatography (SEC-HPLC). Aggregation (measured via SEC-HPLC analysis) and binding (measured using CM5 gold sensor chips) were measured to determine the effect of the antioxidant on aggregation and bioactivity of the therapeutic protein.

The SEC-HPLC conditions were as follows: a G3000 TOSOH SWXL column was used and the flowrate was set at 0.5 mL/min. For EPO, the mobile phase was 100 mM sodium phosphate, 0.5M sodium chloride, pH 6.9, and each sample was run for 80 minutes.

For both IgG1 and IgG2, the mobile phase was 80 mM sodium phosphate, 300 mM sodium perchlorate, 10% isopropanol, pH 7.2, and each sample was run for 45 minutes.

The binding activity of therapeutic protein to a ligand (e.g. to an antibody or binding partner, or, in cases where the therapeutic was an antibody, binding activity to the specific target antigen or to protein A) was determined as follows. Carboxymethyl-dextran chains on a CM5 gold sensor chip were activated with 1-ethyl-3-(3-dimethylaminopropyl)-carbodiimide HCl (EDC) and N-hydroxysuccinimide (NHS) at a flow rate of 5 µL/min. The therapeutic protein-binding ligand of interest was injected until the desired immobilization level was achieved (above 5000 response units). Three different therapeutic protein-binding ligands were measured—Antibody A's target antigen, Protein A, and D11 (an antibody that binds to erythropoietin). For introduction of Antibody A's target antigen to the column, an 80 µg injection of the antigen, diluted in 10 mM Na Acetate pH 4.0 was introduced; for Protein A, a 4 µg injection of Protein A, diluted in 10 mM Na Acetate pH 4.5, was introduced; for D11, a 1 g injection of D11, diluted in 10 mM Na Acetate pH 5.0 was introduced. The remaining activated groups were blocked with 1.0 M ethanolamine-HCl, pH 8.5.

A standard curve was prepared by using native forms of the therapeutic protein of interest. Native forms of the therapeutic protein were diluted in HBS-EP buffer (pH 7.4) to concentrations between 1 and 5 µg/mL, and then injected on the column, prepared as described above to obtain a standard curve. At the end of each sample run, regeneration buffer was used to wash away any bound therapeutic protein in preparation for subsequent injections.

Various UV-stressed antibody formulations were also diluted in HBS-EP buffer (pH 7.4) to a concentration within the standard curve region, and injected to quantitate the loss of bioactivity to its respective ligand-binding partner.

Example 1

Effect of Cinnamic Acid Derivative on Binding Activity of Therapeutic Proteins

The binding activity of various therapeutic proteins in aqueous formulations containing an antioxidant were assessed as described below.

FIG. 1 shows the binding of Antibody A, an IgG1 monoclonal antibody, to its target antigen and protein A. Antibody A was formulated at pH 5.20 in acetate buffer. The exposure of Antibody A to 302 nm UV light caused a decrease in the binding to both of these ligands over the course of 24 hours. This binding was preserved by the addition of antioxidants chlorogenic, ferulic, or coumaric acid at a concentration of 20 mM.

FIG. 2 shows the effect of UV-B exposure on another IgG1 monoclonal antibody, Antibody B. Antibody B is the 1119 antibody of US Patent Application No. US 2005/0004353, which binds specifically to human interferon gamma. The sequence and properties of the 1119 antibody are fully described in US Patent Application No. US 2005/0004353, which is incorporated by reference herein in its entirety. Antibody B was formulated at pH 6.90 in phosphate buffer. The loss of binding to protein A of Antibody B occurred in the formulation with no antioxidant, but addition of 20 mM chlorogenic or ferulic acid prevented UV-B induced degradation. The addition of 20 mM methionine (a non-aromatic additive), however, was not able to prevent this UV-B induced degradation.

Figure 3:
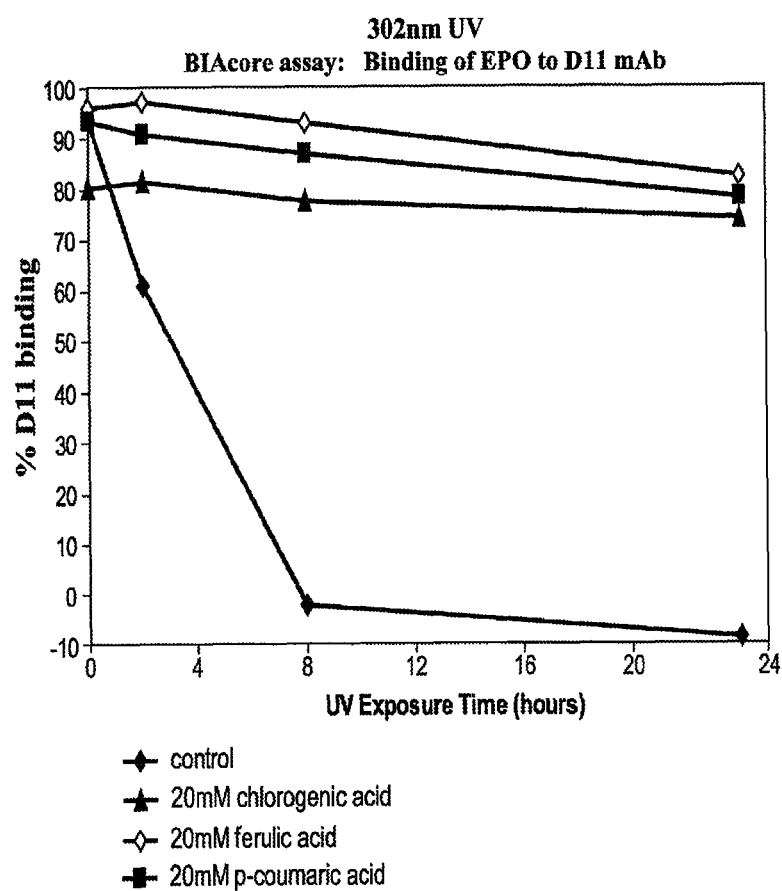
FIG. 3 shows binding of erythropoietin (EPO) to D11 in formulations containing no antioxidant or 20 mM chlorogenic acid, ferulic acid, or coumaric acid, after exposure to 0-24 hours UV radiation.

FIG. 3 shows the results of EPO formulations upon exposure to UV-B radiation. The protein was exposed to the same conditions as Antibody A and Antibody B for up to 24 hours. The integrity of the protein was assessed by its ability to bind to an immobilized monoclonal antibody which recognizes a portion of its active site. The binding of EPO to the D11 mAb was completely eliminated following 24 hours of UV light exposure, in the absence of any antioxidant. The cinnamic acid derivatives—ferulic, chlorogenic, and coumaric acids—formulated at 20 mM were able to significantly preserve the antibody's ability to bind to D11. The protection afforded by these antioxidants is extended to smaller molecular weight proteins as well as monoclonal antibodies.

Example 2

Effect of Cinnamic Acid Derivative on Aggregation of Therapeutic Proteins

The aggregation of various therapeutic protein formulations was assessed in the manner described below.

Figure 5:
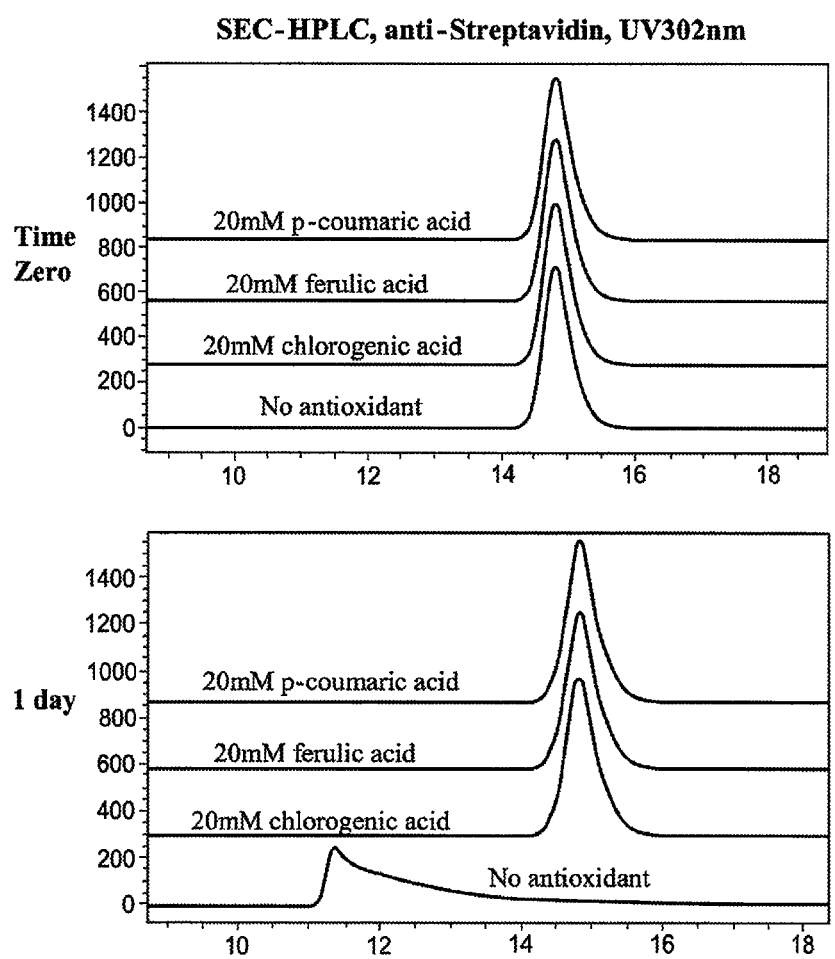
FIG. 5 shows degradation of anti-streptavidin, an IgG2 antibody, in formulations containing no antioxidant or 20 mM chlorogenic acid, ferulic acid, or coumaric acid, after exposure to 24 hours UV radiation.
Figure 6:
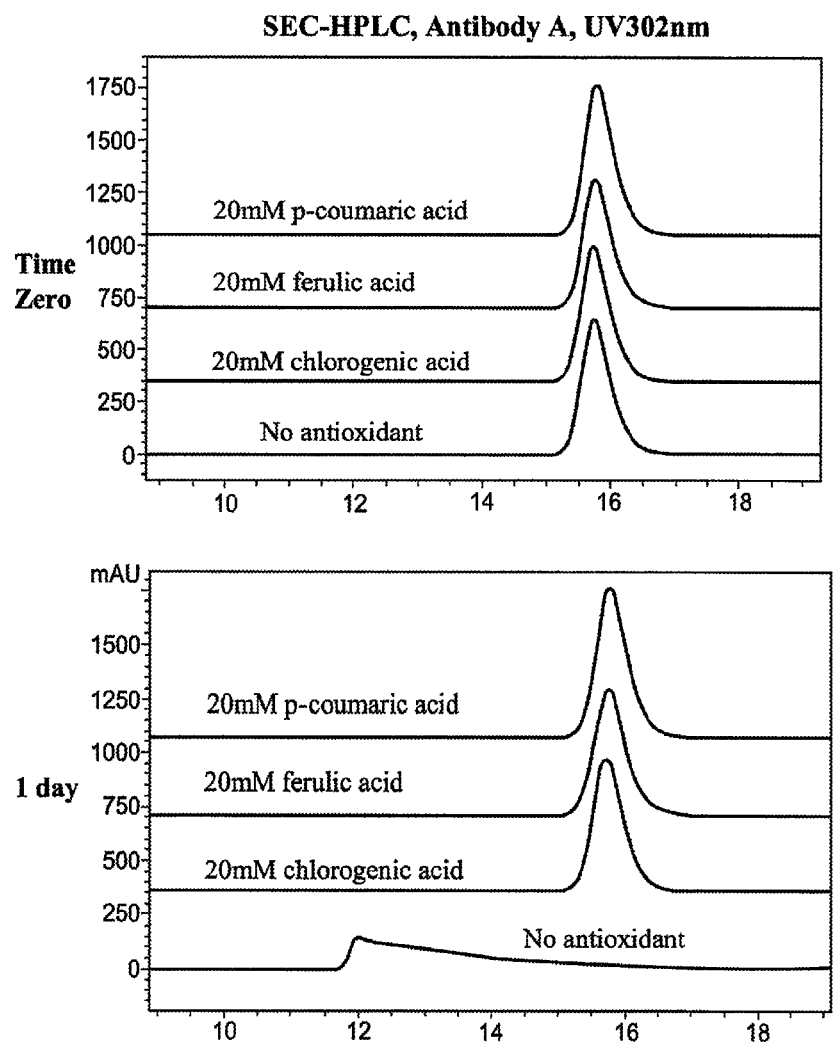
FIG. 6 shows degradation of Antibody A in formulations containing no antioxidant or 20 mM chlorogenic acid, ferulic acid, or coumaric acid, after exposure to 24 hours UV radiation.

FIG. 4 (EPO), FIG. 5 (anti-streptavidin), and FIG. 6 (Antibody A) show SEC-HPLC chromatograms of each proteins following exposure to 302 nm UV-B light for 24 hours. For FIG. 4, the EPO formulation was prepared having the following characteristics: 1 mg/mL EPO, 25 mM sodium phosphate, 125 mM sodium chloride, and pH 6.90. For FIG. 5, the anti-streptavidin formulation was prepared having the following characteristics: 1 mg/mL anti-streptavidin mAb (IgG2), 10 mM sodium acetate, 5% sorbitol, and pH 5.00. For FIG. 6, the Antibody A formulation was prepared having the following characteristics: 1 mg/mL Antibody A (IgG1), 10 mM sodium acetate, 9% sucrose, and pH 5.20.

These figures show the amount of aggregate for each protein formulation is dramatically reduced when the formulation contains 20 mM of a cinnamic acid derivative (chlorogenic, ferulic, or coumaric acid). Aggregation of proteins exposed to UV light typically occurs as a result of tyrosine radical formation leading to dityrosine crosslinking. Several other mechanisms of photo-oxidation can also lead to protein aggregation during UV exposure and these figures show that cinnamic acid derivatives are able to fully inhibit these aggregation mechanisms. The three figures show that cinnamic acid derivatives are able to inhibit the aggregation of a glycosylated helical bundle protein (EPO, FIG. 4), an IgG2 monoclonal antibody (anti-streptavidin, FIG. 5), and an IgG1 monoclonal antibody (Antibody A, FIG. 6). The three figures encompass the pH range of 5.00-6.90 and the addition of excipients 125 mM sodium chloride, 5% sorbitol, and 9% sucrose.

Example 3

Effect of Varying Amounts of Cinnamic Acid Derivatives on Binding Activity and Aggregation of Therapeutic Proteins The efficacy of varying amounts of different antioxidants were assessed in the manner described below.

Figure 7:
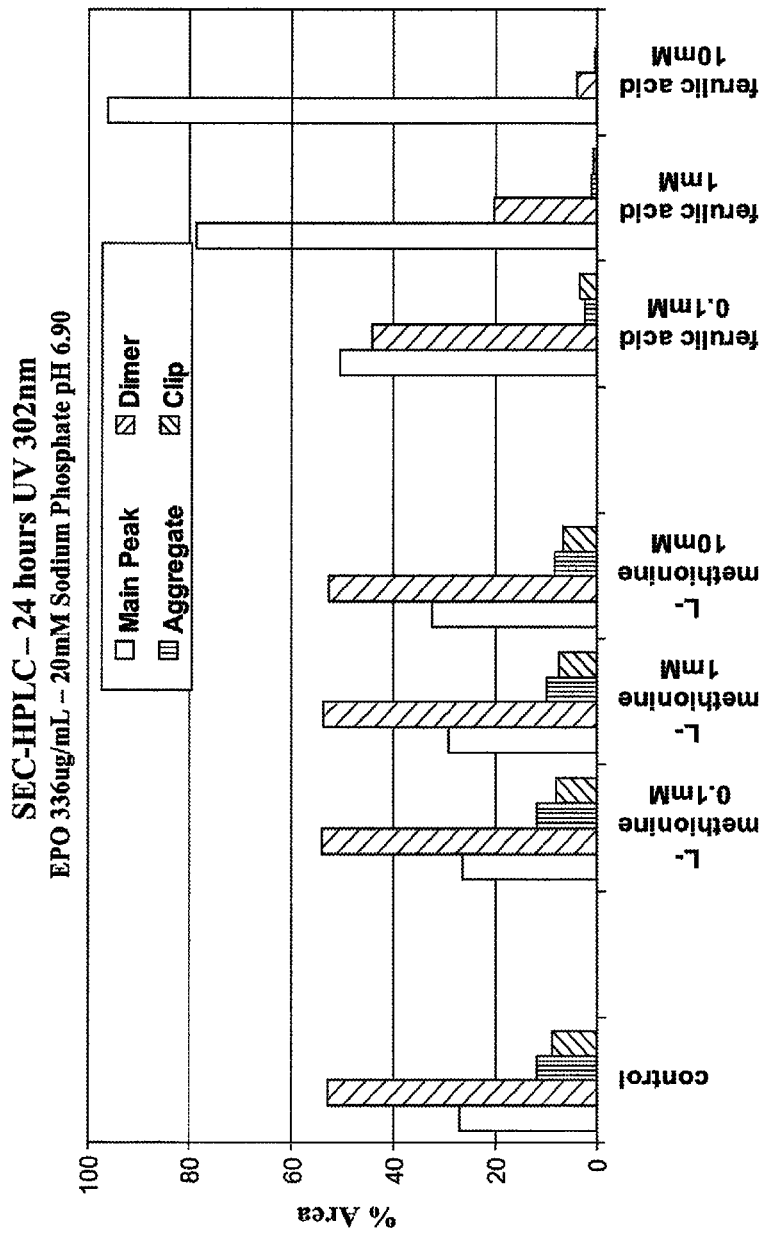
FIG. 7 shows degradation of EPO in formulations containing no antioxidant or 0.1 mM, 1 mM, or 10 mM methionine or ferulic acid, after exposure to 24 hours UV radiation.

FIG. 7 shows SEC-HPLC results for EPO formulations with the following characteristics: 0.336 mg/mL EPO, 20 mM sodium phosphate, and pH of 6.90, 0.1, 10, and 20 mM methionine or ferulic acid were added to the formulation. Each formulation was then exposed to 302 nm UV-B light for 24 hours. The protein formulation was then analyzed using SEC-HPLC. The results showed that ferulic acid at concentrations as low as 0.1 mM were able to reduce the amount of EPO dimer and aggregate caused by UV light exposure. Even 0.1 mM ferulic acid was able to prevent EPO degradation more effectively than 10 mM methionine.

Figure 8:
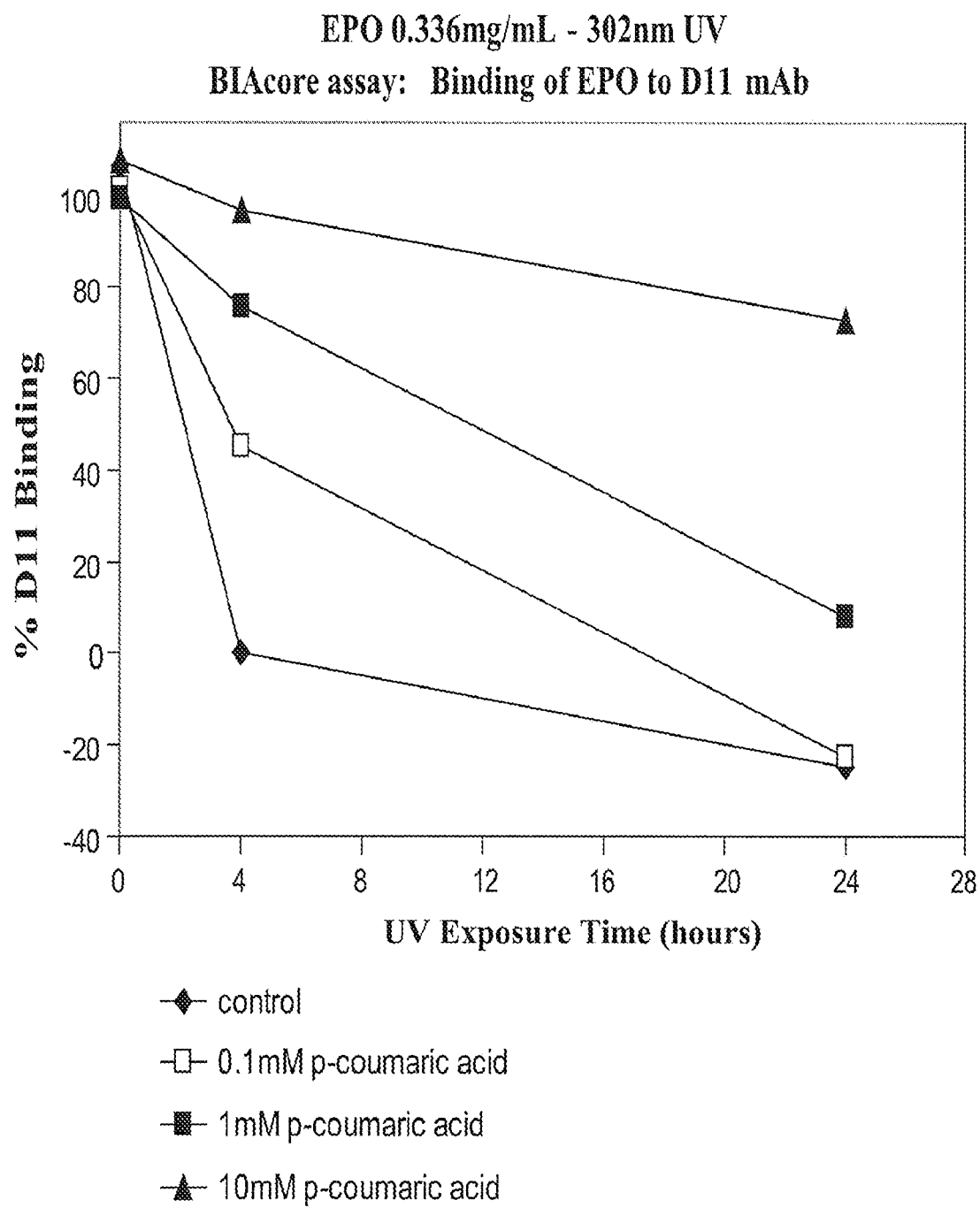
FIG. 8 shows binding of EPO to D11 in formulations containing no antioxidant or 0.1, 1 or 10 mM coumaric acid, after exposure to 0-24 hours UV radiation.

FIG. 8 shows antibody-binding results for EPO formulations having 0, 0.10 mM, 10 mM, or 20 mM coumaric acid between 0 and 24 hours exposure to UV-B radiation. These results showed that 0.1 mM coumaric acid was able to preserve EPO binding to D11 monoclonal antibody for at least 4 hours exposure to UV-B radiation.

Figure 9:
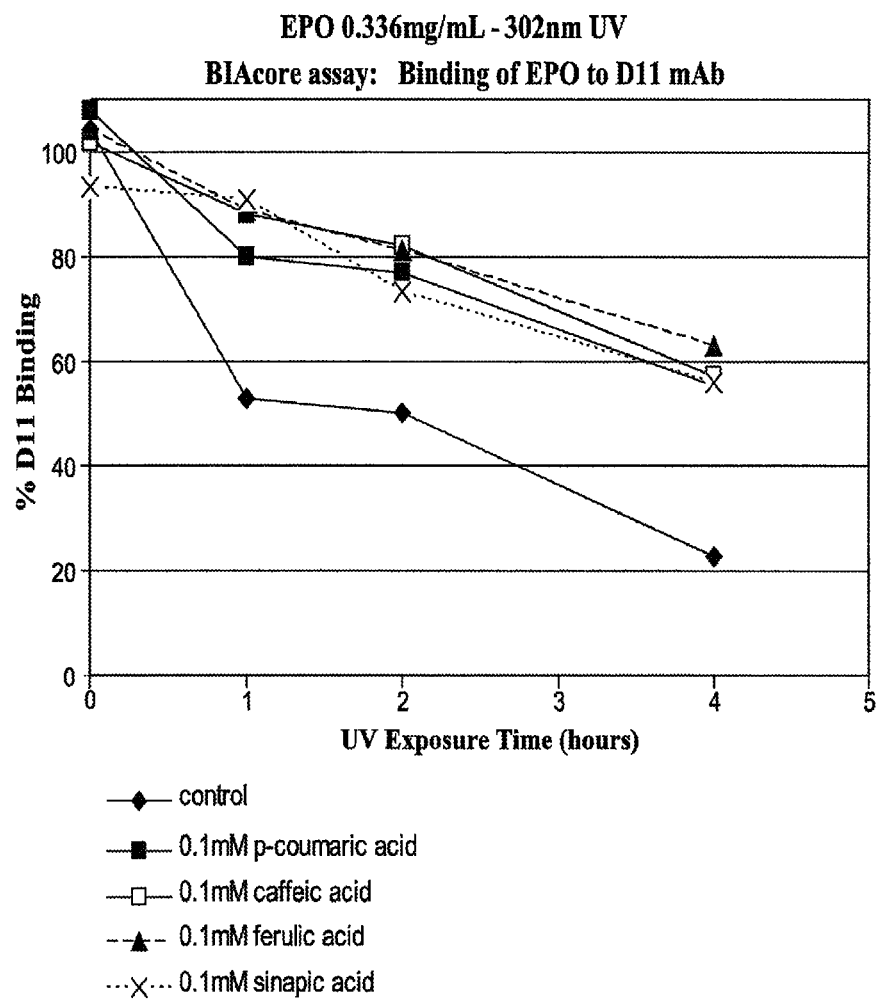
FIG. 9 shows binding of EPO to D11 in formulations containing no antioxidant or 0.1 mM coumaric acid, caffeic acid, ferulic acid, or sinapic acid, after exposure to 0-4 hours UV radiation.

FIG. 9 shows the efficacy of 0.1 mM amount of antioxidants in protecting EPO binding activity to D11. Formulations containing 40 kU/mg EPO were prepared with no antioxidant or with 0.1 mM coumaric, ferulilc, sinapic, or caffeic acid, and exposed to UV-B radiation for up to 24 hours. The binding activity of EPO in each formulation was measured at various time points. FIG. 9 shows that each of the antioxidants at 0.1 mM was able to protect the EPO from degradation and preserve its binding activity during the UV-B exposure.

Figure 10:
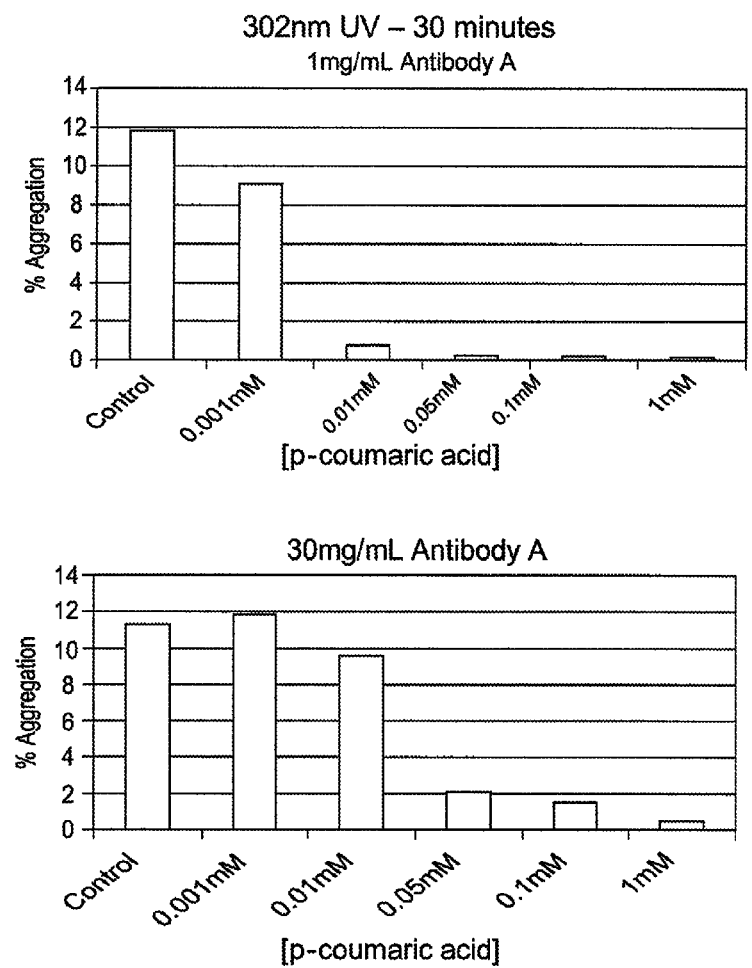
FIG. 10 shows aggregation of Antibody A (1 mg/mL—top; 30 mg/mL —bottom) in formulations containing no antioxidant or 0.001 mM, 0.01 mM, 0.05 mM, 0.1 mM, or 1 mM coumaric acid.

FIG. 10 shows protein formulations of 1 mg/mL (FIG. 10, top) Antibody A having concentrations of coumaric acid as low as 0.001 mM (1 μM) are effective in reducing the amount of aggregate formed when exposed to UV-B for 30 minutes. FIG. 10 also shows that higher concentrations of coumaric acid are necessary for a 30 mg/mL formulation or even 30 mg/mL (FIG. 10, bottom), but that 0.01 mM still prevents aggregation of Antibody A better than no antioxidant at all (i.e., control). Formulations containing lower concentrations of hydrophobic antioxidants are advantageous because lower concentrations are less likely to cause protein denaturation which could lead to aggregation and precipitation at higher temperatures.

Example 4

Effect of Combinations of Antioxidant and Osmolyte on Aggregation of Therapeutic Proteins The following formulations were prepared to assess the combination of antioxidant and osmolyte in increasing the stability of a therapeutic protein formulation. Previous work has shown that osmolytes protect proteins from thermal denaturation and aggregation caused by preservatives which are similar in structure and effect to the cinnamic acid derivatives.

Figure 11:
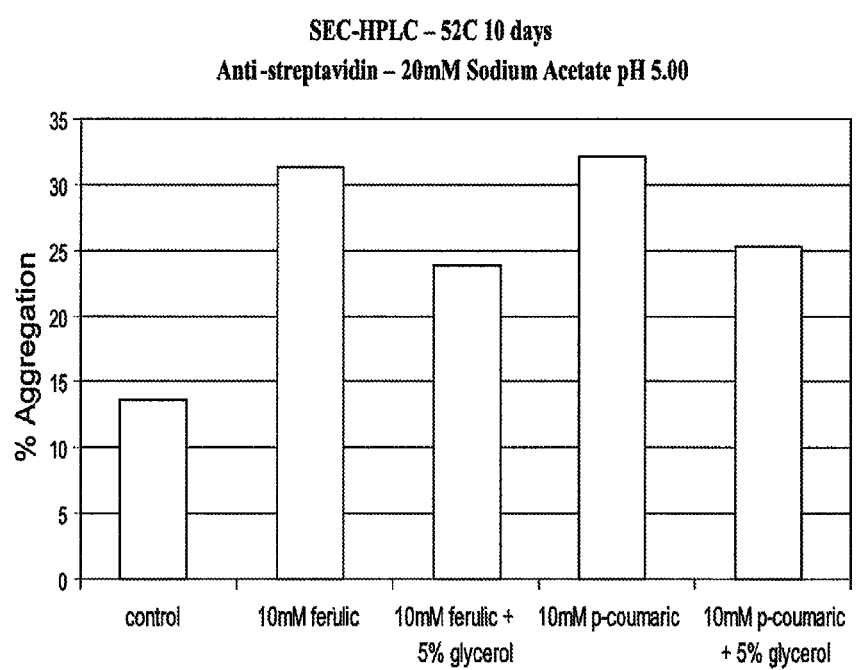
FIG. 11 shows aggregation of anti-streptavidin, an IgG2 antibody, after 10 days at 52° C. in formulations containing no antioxidant or 10 mM ferulic acid or 10 mM coumaric acid with and without 5% glycerol.

FIG. 11 shows that glycerol reduced the effect of ferulic and p-coumaric acids on the aggregation of an IgG2 antibody at 52° C. for 10 days. Anti-streptavidin was formulated in 50 mM sodium acetate at pH 5.00. These formulations were not exposed to UV radiation but assessed on their thermal stability. As seen in FIG. 11, ferulic acid and coumaric acid contributed to the aggregation of anti-streptavidin after 10 days at 52° C.; the addition of 5% glycerol counter-acted that thermal aggregation.

Example 5

Figure 12:
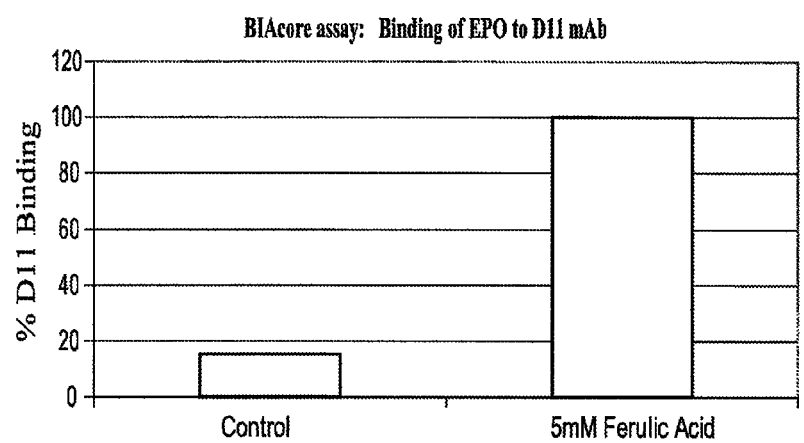
FIG. 12 shows binding of EPO to D11 in formulations containing no antioxidant or 5 mM ferulic acid after exposure of 0.3% $H_2O_2$, 0.2 mM Fe-EDTA, and 1 mM ascorbic acid for 2 hours.

Effect of Antioxidant on Therapeutic Proteins Exposed to Free Radicals Generated from Metal Ions Proteins may be oxidized through a variety of other mechanisms besides exposure to ultraviolet light, including the generation of hydroxyl radicals mediated by metal ions. In order to assess the ability of antioxidants to protect proteins from this type of oxidation, formulations of EPO (336 μg/mL), with and without 5 mM ferulic acid, in HBS at pH 7.0 were exposed to oxidation from a solution of 0.2 mM Fe-EDTA, 0.3% $H_2O_2$, and 1 mM ascorbate for 2 hours at 37° C. FIG. 12 shows that ferulic acid was able to protect EPO from this type of metal catalyzed oxidation, and preserved 100% of EPO binding activity compared to a sample with no antioxidant which retained less than 20% of its activity under the same conditions.

Example 6

Effect of Antioxidant on Discoloration of Therapeutic Proteins

Proteins may also become yellow in color following exposure to UV light. This yellowing is most likely caused by oxidation of tryptophan residues in the protein. To assess the ability of various antioxidants to protect against this yellowing, formulations of Antibody A were prepared with no antioxidant, 10 mM methionine, 10 mM ferulic acid (alone or in the presence of 10 mM methionine), 10 mM coumaric acid (alone or in the presence of 10 mM methionine), and 5 mM coumaric acid in the presence of 10 mM methionine. The control formulation showed significant yellowing after exposure to UV-B light for 24 hours, as did the 10 mM methionine formulation. However, the rest of the formulations, each containing an antioxidant, showed no appreciable yellowing after exposure to 24 hours of UV-B light.

Example 7

Effect of Benzoic Acid Derivatives on Aggregation of Therapeutic Proteins

Figure 13:
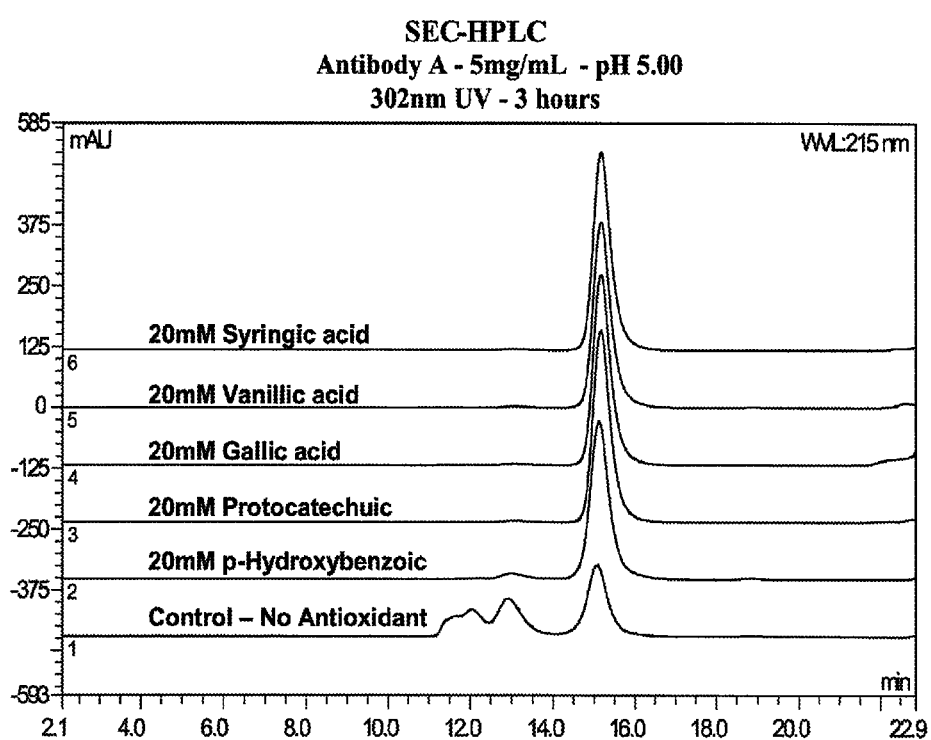
FIG. 13 shows degradation of Antibody A in formulations containing no antioxidant or 20 mM syringic acid, vanillic acid, gallic acid, protocatechuic acid, or p-hydroxybenzoic acid, after exposure to UV radiation for 3 hours.

Benzoic acid derivatives were assessed as possible antioxidants for therapeutic protein formulations. FIG. 13 shows the SEC-HPLC aggregates of various formulations of Antibody A (5 mg/mL) in 20 mM sodium acetate at pH 5.00 alone or in the presence of 20 mM syringic, vanillic, gallic, protocatechuic, or p-hydroxybenzoic acid, upon exposure to UV-B radiation at 4° C. for 3 hours. Each of the benzoic acid derivatives was able to significantly decrease the amount of aggregation due to the radiation, as compared to the control formulation.

Figure 14:
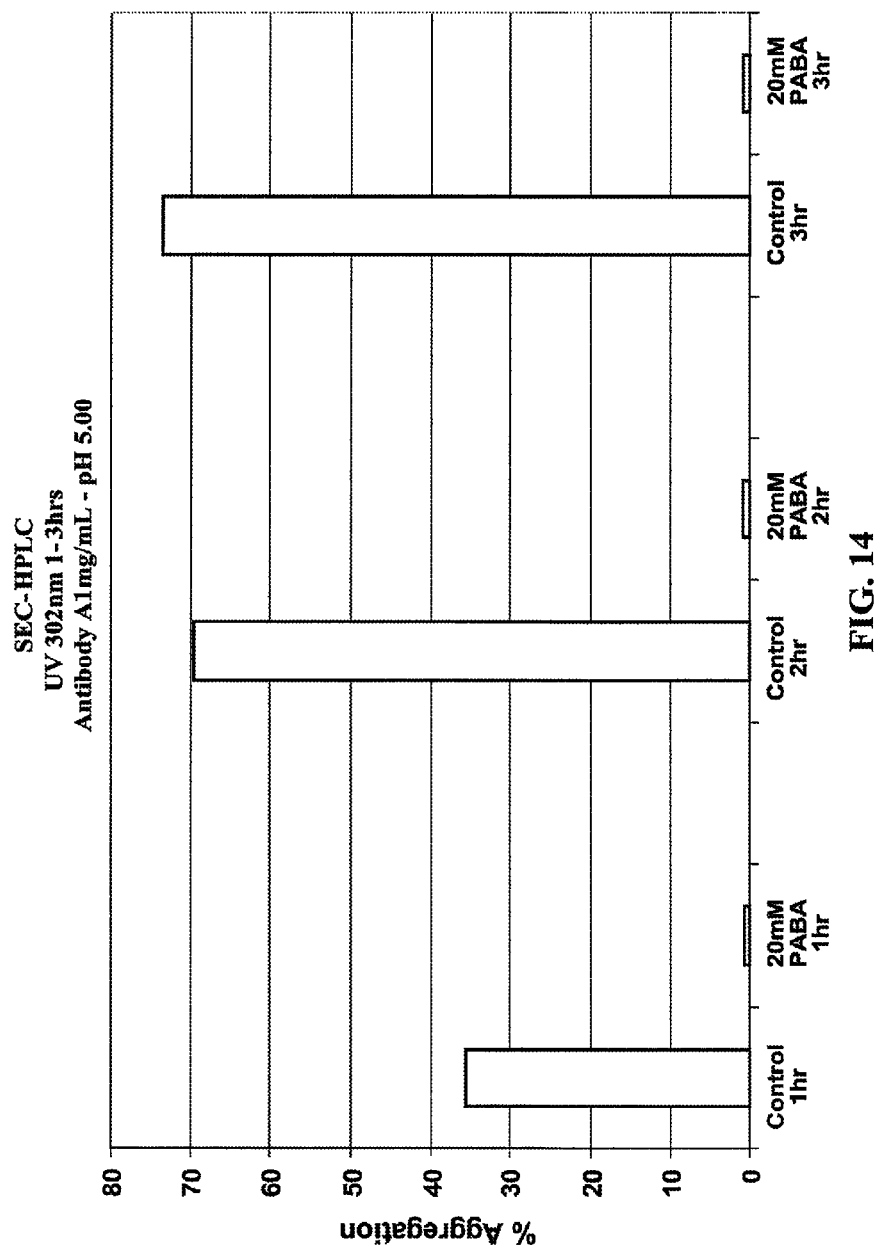
FIG. 14 shows aggregation of Antibody A in formulations containing no antioxidant or 20 mM p-aminobenzoic acid, after exposure to UV radiation for 1,2, and 3 hours.

P-amino benzoic acid (PABA) has a relatively powerful antioxidant effect. PABA, like pyridoxine, changes to an orange-brown color upon light. PABA is commonly used as a sunscreen additive, but was found to cause skin irritation in some people and has since been discontinued. It may be safe for use in parenteral formulations, however, and it has been tested in clinical trials for a variety of ailments and is often given to humans in doses as high as 12 grams per day without significant toxicity. Formulations of Antibody A (1 mg/mL) at pH 5.00 with and without 20 mM PABA were exposed to UV radiation for 1, 2, or 3 hours and the aggregation was measured using SEC-HPLC. PABA was able to significantly reduce the amount of aggregation of Antibody A at all three time points (FIG. 14).

Figure 15:
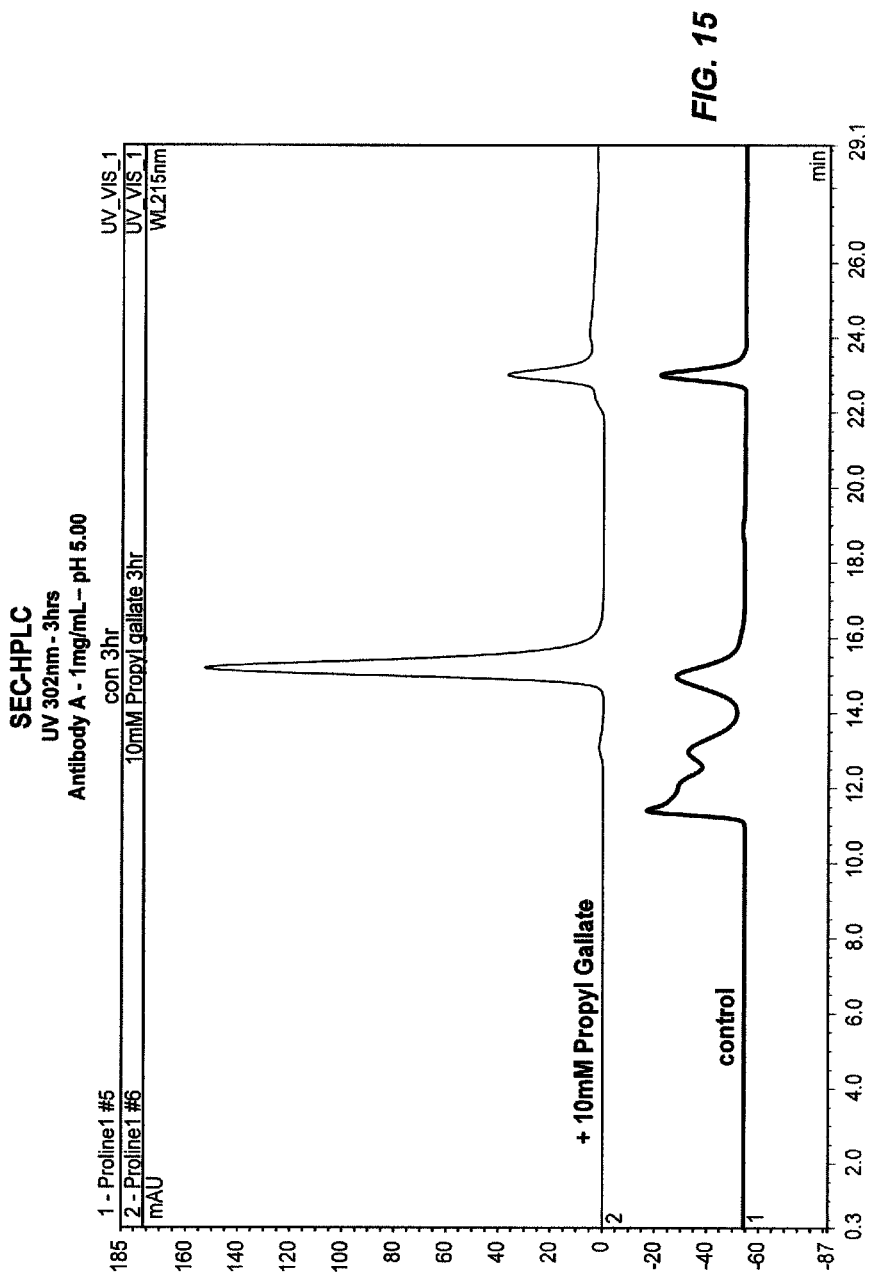
FIG. 15 shows degradation of Antibody A in formulations containing no antioxidant or 10 mM propyl gallate, after exposure to UV radiation for 3 hours.

The effect of propyl gallate as an antioxidant was also assessed. Formulations of Antibody A at pH 5.00 in the presence or absence of 10 mM propyl gallate were exposed to UV radiation for 3 hours. The aggregation of Antibody A was then measured using SEC-HPLC. Propyl gallate was able to significantly reduce the amount of aggregation of Antibody A due to radiation (FIG. 15). Propyl gallate is commonly used as a food and cosmetic additive and is listed as an ingredient in the multidose formulation of Terramycin for intramuscular injection. Its concentration in Terramycin is listed as 0.02%, which corresponds to a concentration of about 1 mM.

Example 8

Effect of Vitamins on Aggregation of Therapeutic Proteins

Figure 16:
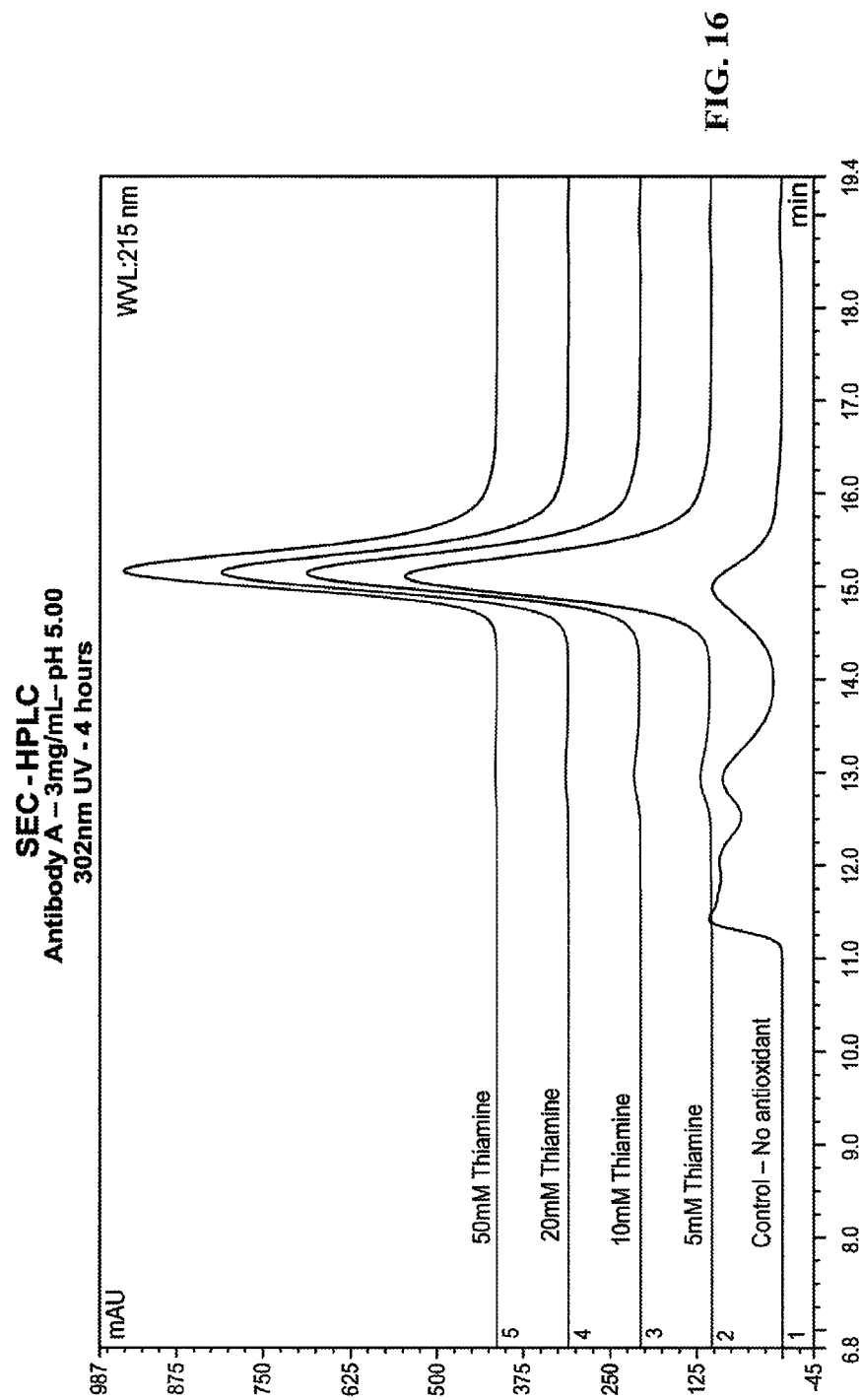
FIG. 16 shows degradation of Antibody A in formulations containing no antioxidant or 5, 10, 20, or 50 mM thiamine, after exposure to UV radiation for 4 hours.

Other aromatic compounds are assessed as possible antioxidants for protein formulations. FIG. 16 shows the effect of adding thiamine-HCl (5, 10, 20, or 50 mM) to Antibody A (3 mg/mL) formulations exposed to UV-B radiation for 4 hours. Thiamine concentrations as low as 5 mM were able to significantly inhibit Antibody A aggregation as measured by SEC-HPLC. Thiamine is also known as vitamin B1, and functions in humans as a cofactor for enzymes involved in carbohydrate metabolism. It is found in meats as well as wheat, rice bran, and fortified bread and cereals. It is less potent in its UV protective effects than the cinnamic acids but is more soluble than the cinnamic acids or the benzoic acid derivatives, and may have less of a denaturing effect on protein thermal stability. It has no known toxicity and although it has not been used in protein formulations, it is routinely used by intravenous injection to treat thiamine deficiency.

Figure 17:
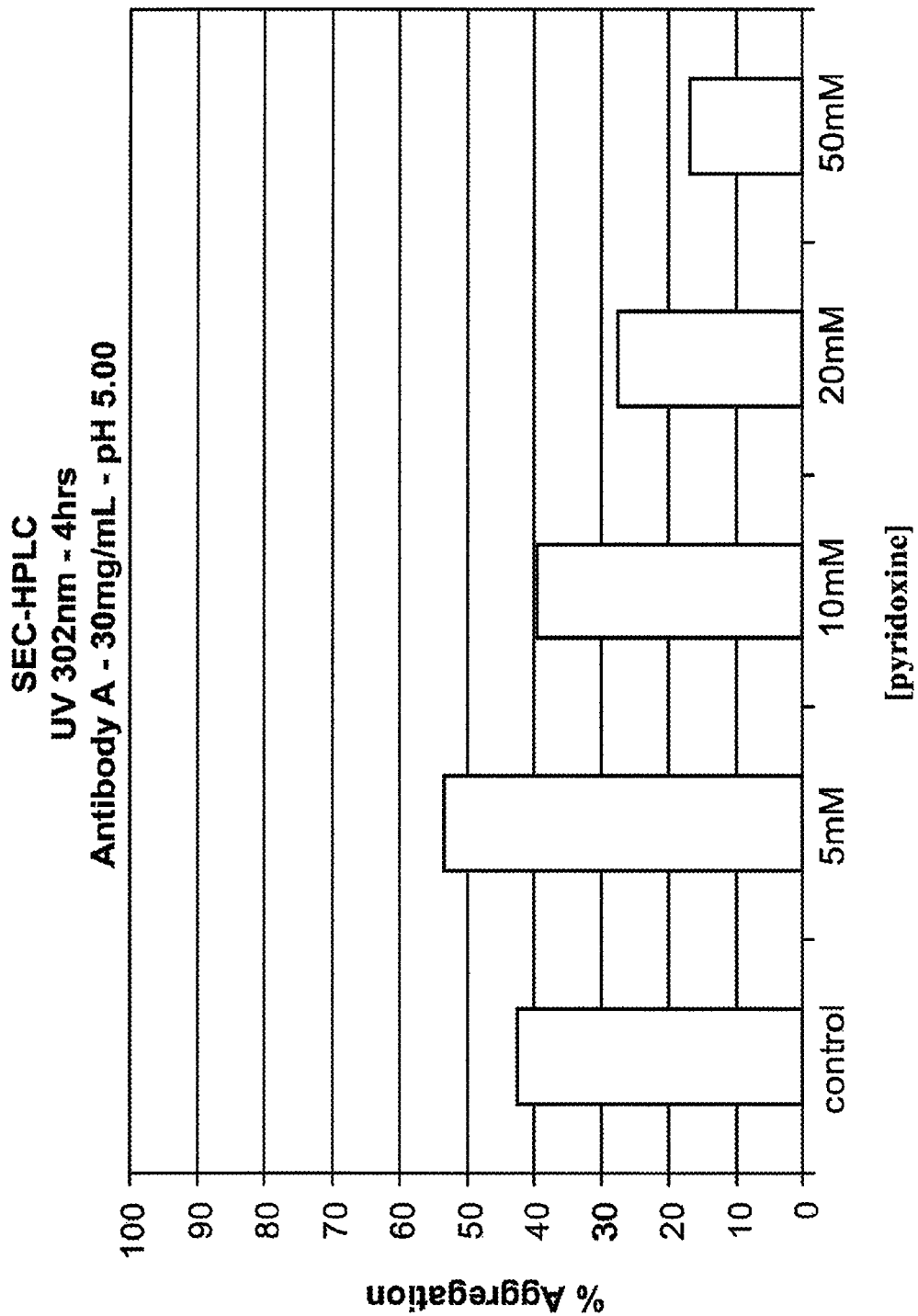
FIG. 17 shows aggregation of Antibody A in formulations containing no antioxidant or 5, 10, 20, or 50 mM pyridoxine, after exposure to UV radiation for 4 hours.

Pyridoxine is another water soluble B-vitamin (B6) which was studied as a possible antioxidant for preventing protein aggregation caused by UV-B exposure. FIG. 17 shows the effect of added pyridoxine (5, 10, 20, or 50 mM) on prevention of antibody aggregation (Antibody A 30 mg/mL) after 4 hours UV-B exposure. Both 20 mM and 50 mM pyridoxine did protect the protein from oxidation and aggregation, but also caused the formulation to appear yellow, upon exposure to UV radiation. Pyridoxine may be useful in protein formulation despite this yellowing. It is highly soluble and injections of pyridoxine are commonly given to humans to correct deficiencies so it is expected to be non-toxic.

Example 9

Effect of Antioxidant Preservatives on Aggregation of Therapeutic Proteins

Figure 18:
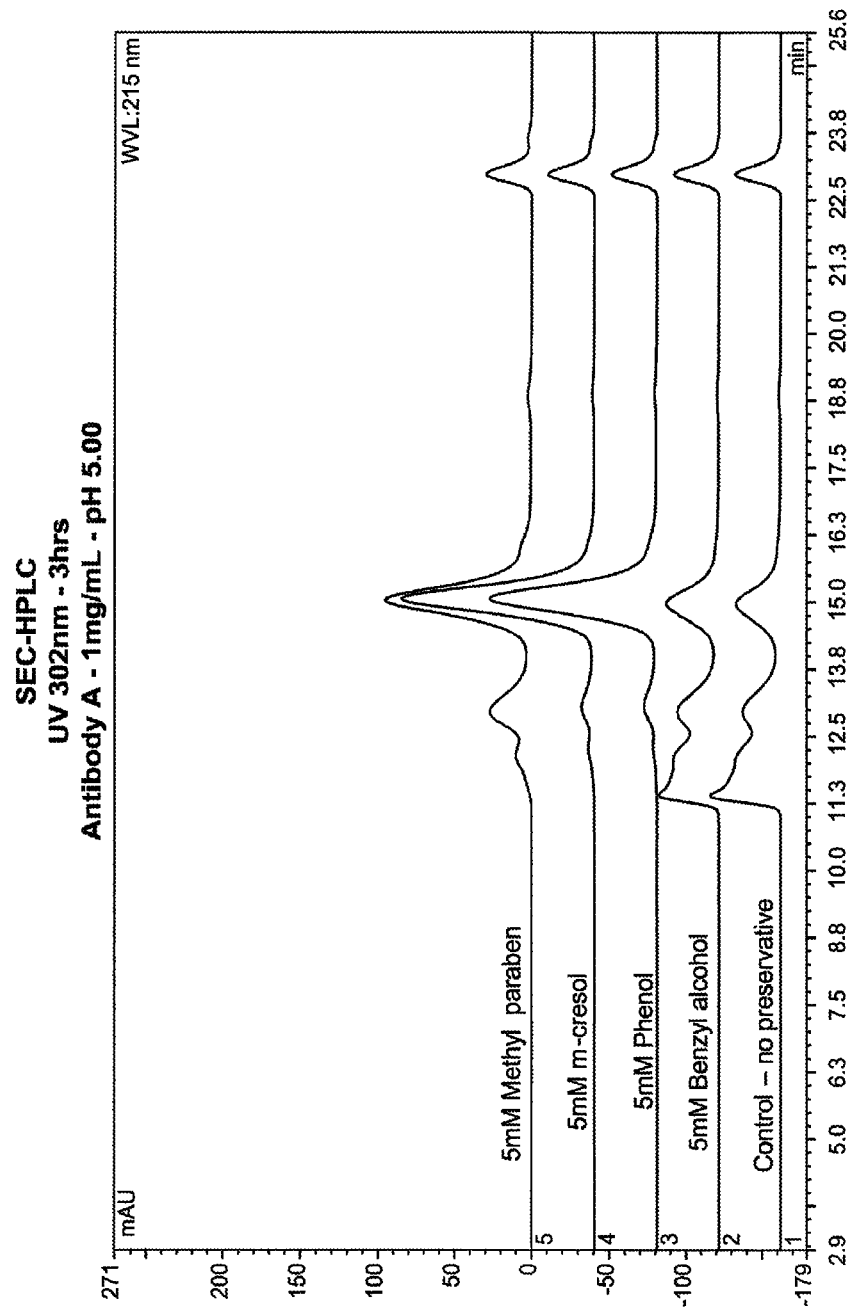
FIG. 18 shows degradation of Antibody A in formulations containing no antioxidant or 5 mM methyl paraben, m-cresol, phenol, or benzyl alcohol, after exposure to UV radiation for 3 hours.
Figure 19:
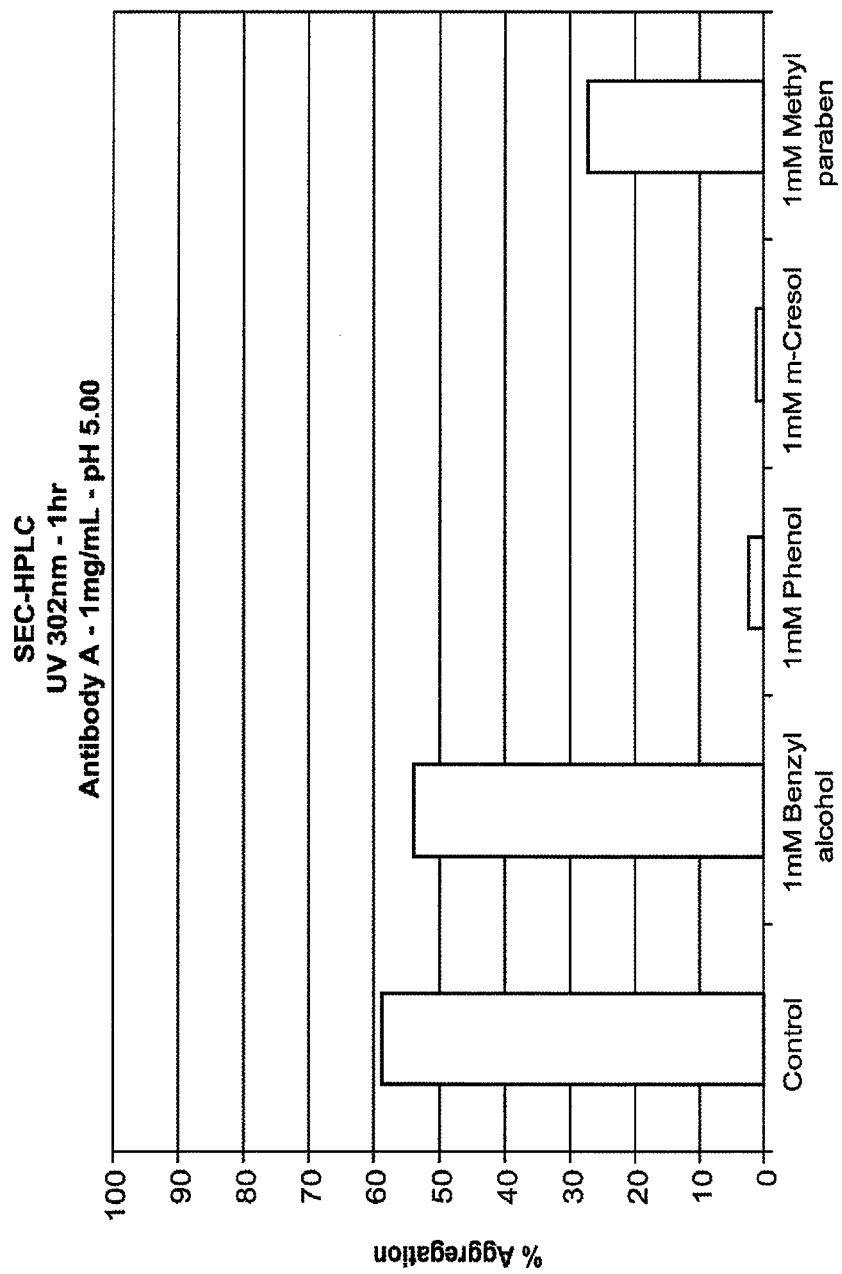
FIG. 19 shows aggregation of Antibody A in formulations containing no antioxidant or 1 mM methyl paraben, m-cresol, phenol, or benzyl alcohol, after exposure to UV radiation for 1 hour.

Preservatives are routinely used in parenteral protein formulations to prevent microbial growth in multidose formulations. However, many preservatives are aromatic and can act as antioxidants at concentrations well below those that are effective for preservatives. Several formulations of Antibody A (1 mg/mL) at pH 5.00 were prepared in the presence of 5 mM or 1 mM benzyl alcohol, methyl paraben, m-cresol, or phenol. The formulations were exposed to UV radiation for 3 hours and the amount of aggregation of Antibody A was measured by SEC-HPLC. The results are shown in FIG. 18 (5 mM) and FIG. 19 (1 mM). Both 1 mM and 5 mM are below the effective preservative amounts of each of these compounds to act as a preservative. This concentration is below that typically used for all of the preservatives shown above. Both cresol and phenol were able to significantly decrease the amount of aggregation of Antibody A upon UV radiation.

Example 10

Figure 20:
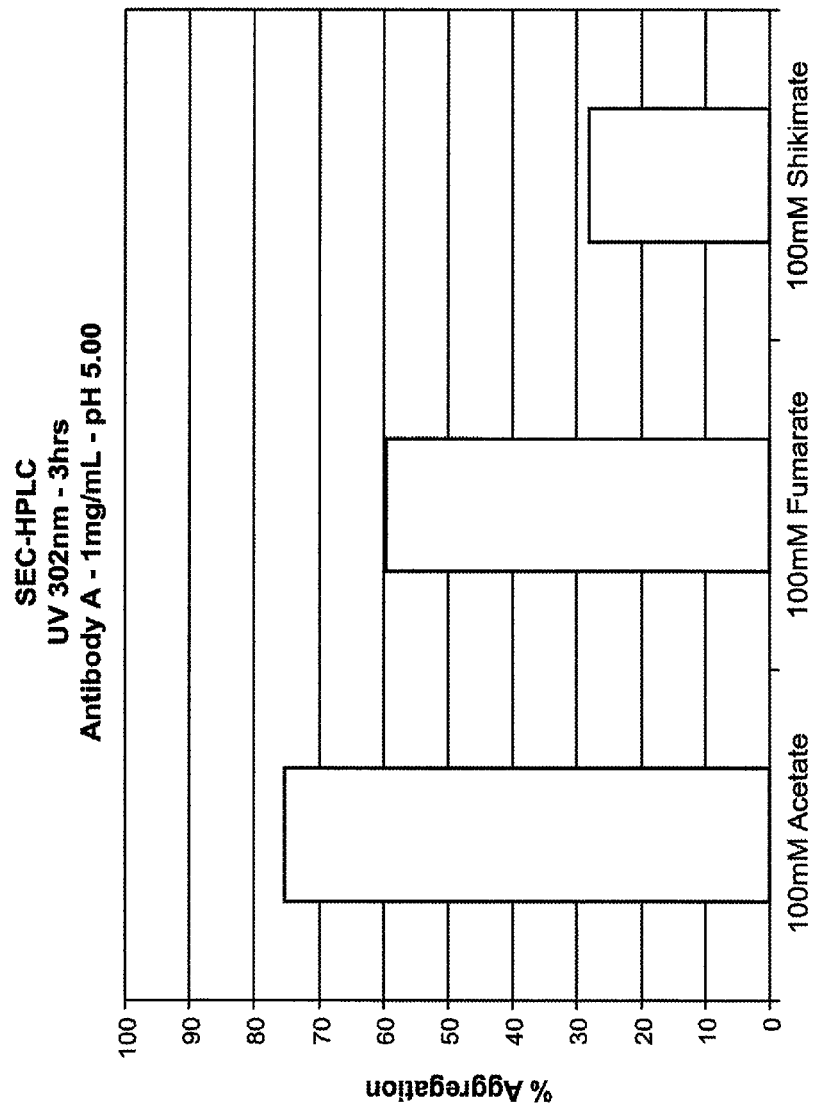
FIG. 20 shows degradation of Antibody A in formulations containing no antioxidant or 100 mM fumaric acid or shikimic acid, after exposure to UV radiation for 3 hours.

Effect of Non-Aromatic Conjugated Compounds on Aggregation of Therapeutic Proteins Compounds having conjugated double or triple bonds may be effective antioxidants. To test this, formulations of Antibody A (1 mg/mL) at pH 5.00 were prepared in the presence and absence of 100 mM fumaric acid or shikimic acid. Each formulation was then exposed to 3 hours UV radiation and the amount of aggregation of Antibody A was measured by SEC-HPLC. Both fumaric acid and shikimic acid were able to protect Antibody A from aggregation (FIG. 20). These compounds also have buffering capacity in the range of pH 4-6 and can be used as antioxidant buffers in protein formulations in this range.

Example 11

Effect of Nucleobases on Aggregation of Therapeutic Proteins

Figure 21:
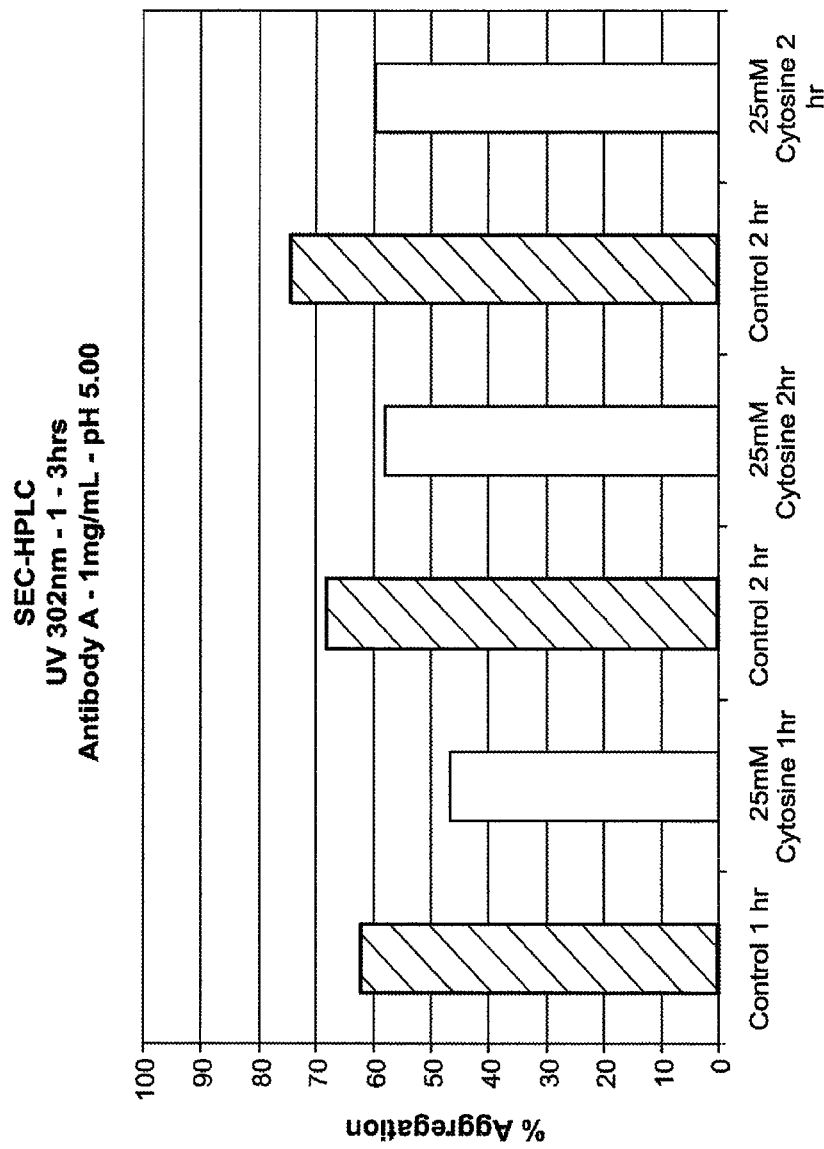
FIG. 21 shows aggregation of Antibody A in formulations containing no antioxidant or 25 mM cystosine after exposure to UV radiation for 1, 2, and 3 hours.

Cytosine is a pyrimidine base and is one of the four major building blocks of DNA. FIG. 21 shows that it is able to prevent aggregation of formulations of Antibody A (1 mg/mL) at pH 5.00 upon exposure to 1, 2, or 3 hours UV radiation.

Other pyrimidine or purine bases, such as adenine, thymine, uracil, or guanine or their corresponding nucleosides and nucleotides and deoxynucleotides are tested as well.

Example 12

Effect of Amino Acids

The protective ability of various amino acids was also measured.

Figure 22:
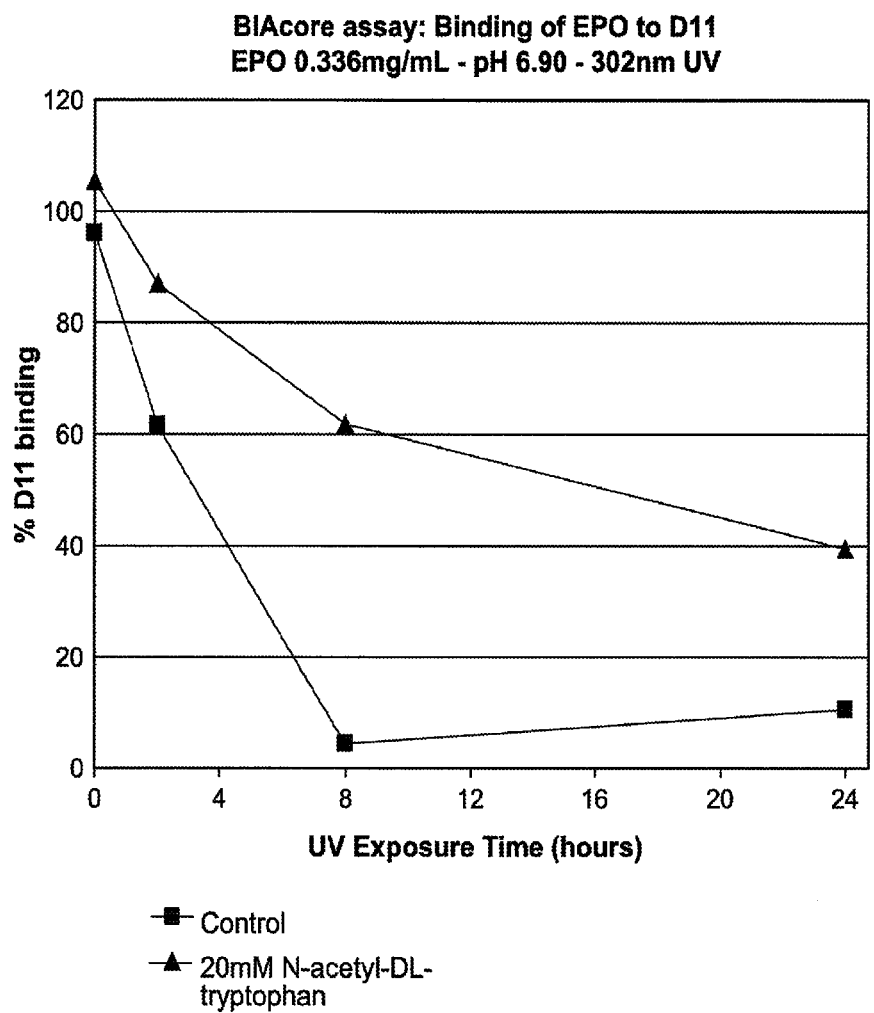
FIG. 22 shows binding of EPO to D11 in formulations containing no antioxidant or 20 mM N-acetyl-tyrptophan, after exposure to UV radiation for 0-24 hours.

Formulations of tryptophan, proline, or methionine were prepared. FIG. 22 shows activity of formulations of 40 kU/mL EPO at pH 6.90 with or without 20 mM racemic N-acetyl-tryptophan after exposure to UV radiation from 0 to 24 hours. EPO activity was preserved from UV-B degradation in the presence of N-acetyl-tryptophan. N-acetyl tryptophan is more soluble than free tryptophan and is used in parenteral formulations of Human Serum Albumin (HSA).

Figure 23:
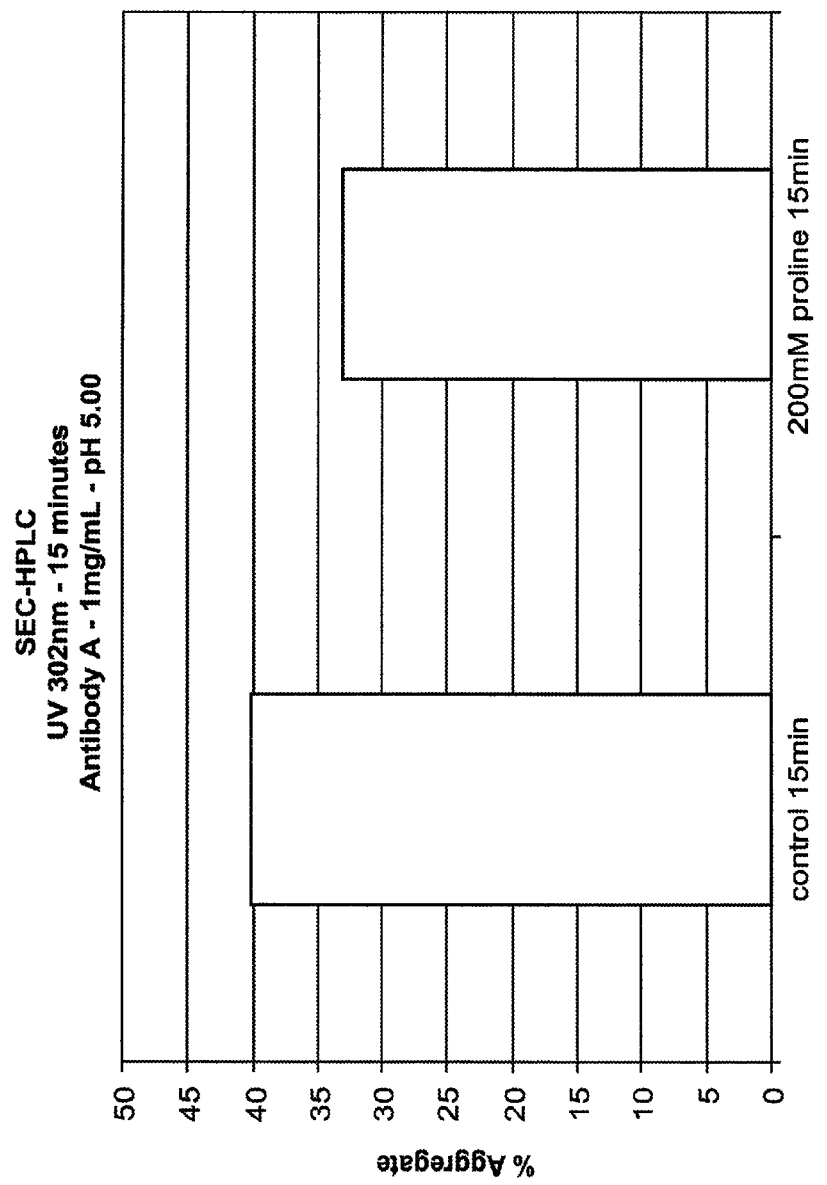
FIG. 23 shows aggregation of Antibody A in formulations containing no antioxidant or 200 mM proline, after exposure to UV radiation for 15 minutes.
Figure 24:
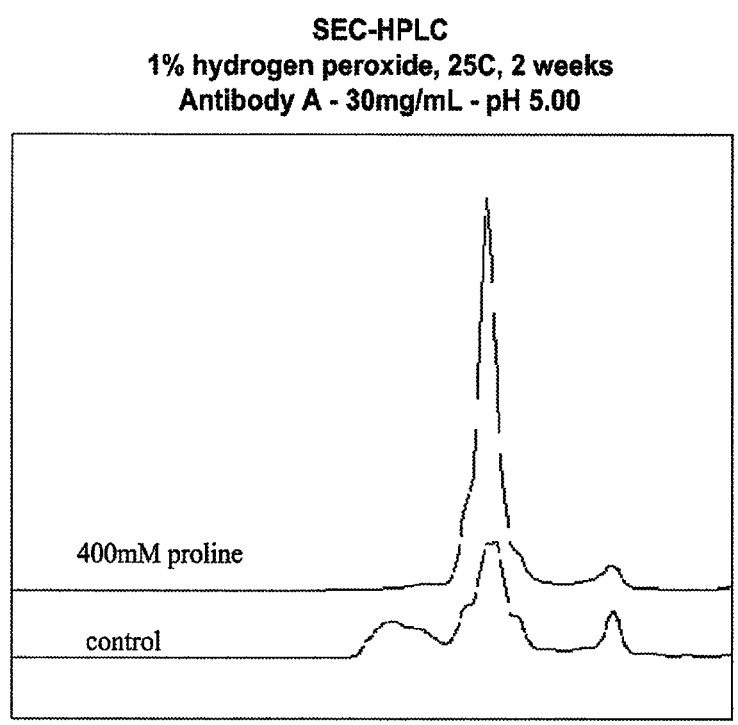
FIG. 24 shows degradation of Antibody A in formulations containing no antioxidant or 400 mM proline, after exposure to a 1% $H_2O_2$ solution at 25° C. for 2 weeks.

Proline is an amino acid that has been known to possess singlet oxygen and free radical scavenging ability due to the properties of its pyrrolidine ring. Aggregation of formulations of Antibody A (1 mg/mL) at pH 5.00 in the presence or absence of 200 mM proline after exposure to UV radiation for 15 minutes showed that proline had a weak effect in protecting a monoclonal antibody from UV-B induced degradation (FIG. 23). However, a stronger effect in preventing antibody aggregation caused by exposure to peroxide was seen when aggregation of Antibody A was measured after exposure to 1% $H_2O_2$ after 2 weeks in the presence or absence of 400 mM proline (FIG. 24).

Figure 25:
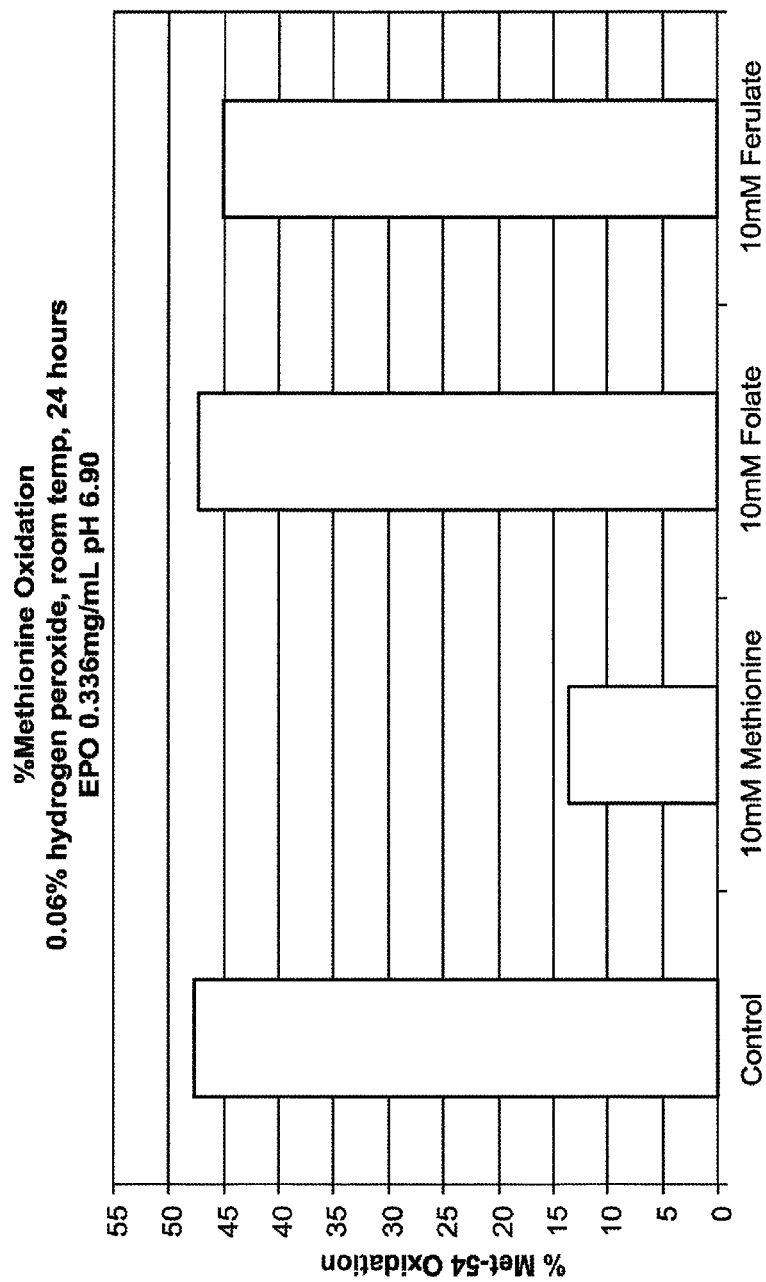
FIG. 25 shows amount of Met-54 oxidation of Antibody A in formulations containing no antioxidant or 10 mM methionine, folic acid, or ferulic acid, after exposure to a solution of 0.06% $H_2O_2$ at room temperature for 24 hours.

Methionine has been previously studied and is well known for its protective effects in preventing protein oxidation under various conditions, its inclusion in protein formulations in combination with antioxidants has not been previously reported. Formulations having methionine and an antioxidant protect the therapeutic protein from both peroxide oxidation and UV radiation oxidation. Formulations of EPO with 10 mM methionine, folic acid, or ferulic acid were exposed to 0.06% $H_2O_2$ for 24 hours at room temperature. The amount of Met-54 oxidation was measured and it was found that 10 mM methionine was able to reduce the amount of EPO oxidation versus that of control or of either of the other two formulations (FIG. 25)

Example 13

Effect of Alpha-Hydroxy Acids on Aggregation of Therapeutic Proteins

Figure 26:
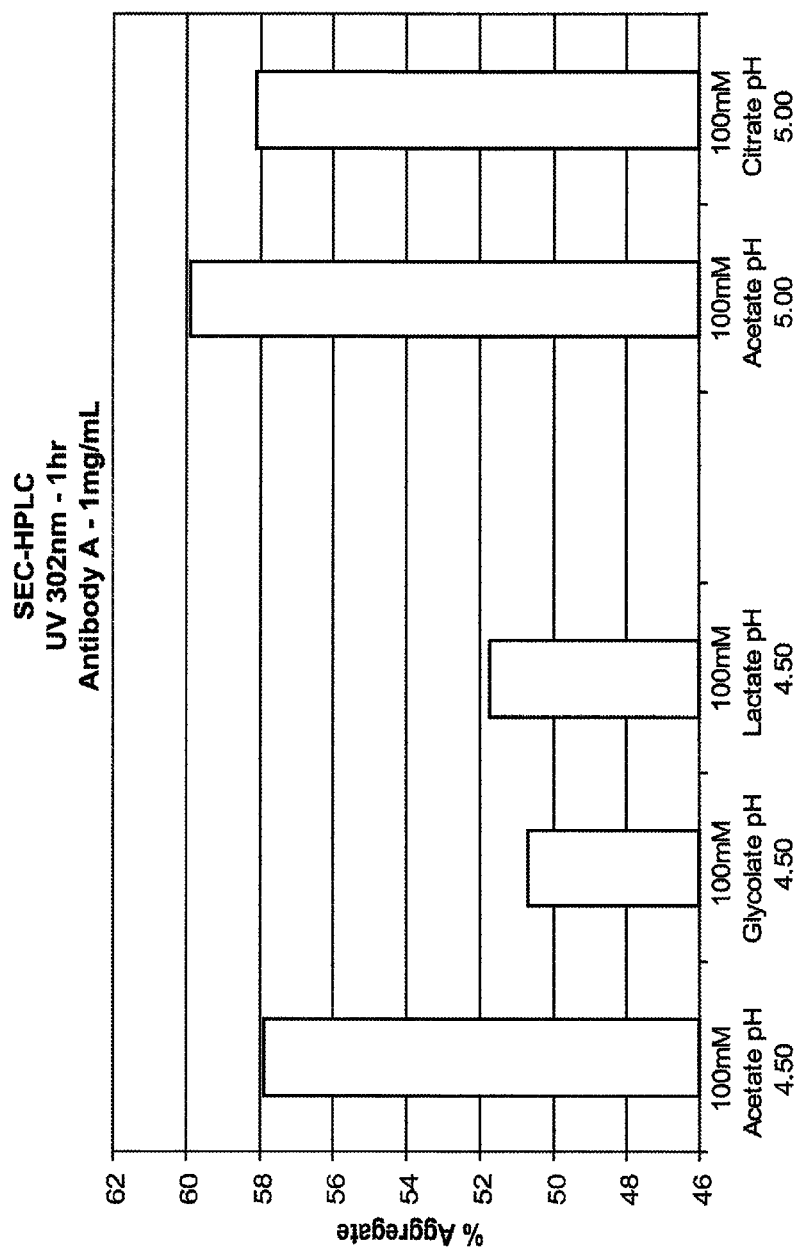
FIG. 26 shows aggregation of Antibody A in formulations containing no antioxidant or 100 mM glycolic acid or lactic acid at pH 4.5 or 100 mM citric acid at pH 5.00, after exposure to UV radiation for 1 hour.

Alpha-hydroxy acids have also been identified as antioxidants. Formulations of Antibody A (1 mg/mL) at pH 4.50 were prepared in the presence of 100 mM glycolic acid or lactic acid or at pH 5.00 with citric acid. The formulations were then exposed to UV radiation for 1 hr and the aggregation of Antibody A was measured using SEC-HPLC (FIG. 26). These compounds are highly soluble at pH 4-5, which is not true for many of the phenolic acids. Glycolic acid is to be the most effective at UV-B protection, while citric acid is fairly weak.

Example 14

Figure 27:
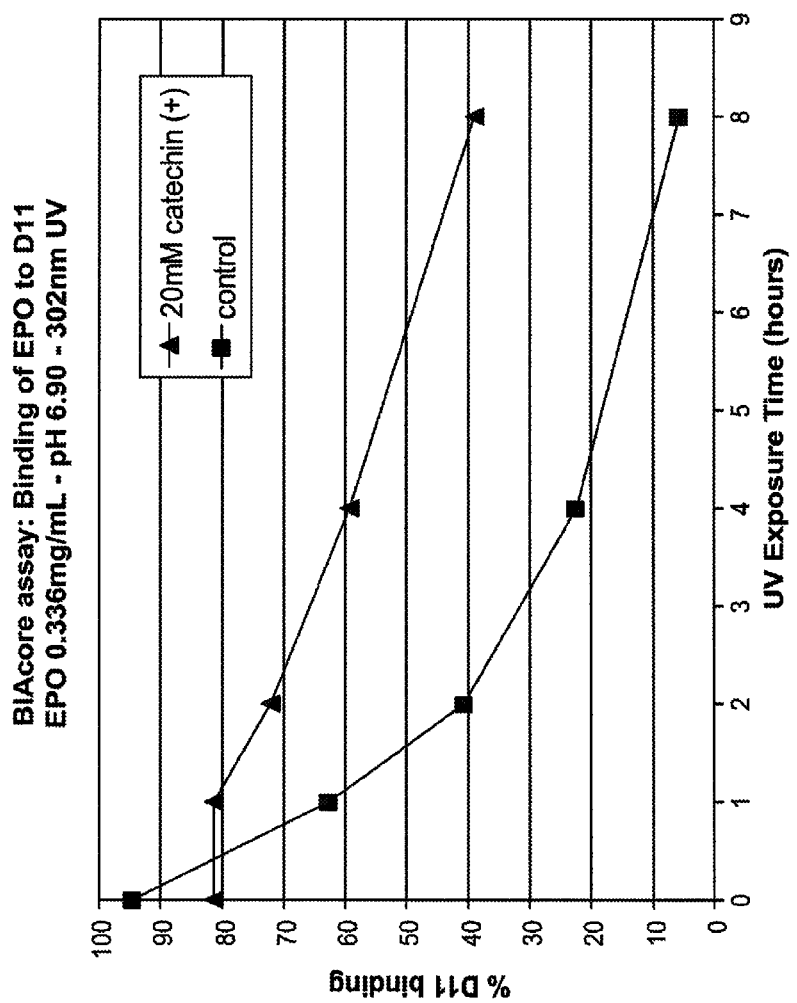
FIG. 27 shows binding of EP0 to D11, in formulations containing no antioxidant or 20 mM catechin, after exposure to UV radiation for 0-8 hours.

Effect of Flavonols and Other Phytochemicals on Binding Activity of Therapeutic Proteins Catechin and epicatechin are stereoisomers that are found in green tea. They are thought to be largely responsible for the high antioxidant capacity of green tea. They are members of the class of compounds called flavonols which are widely distributed in plants and are known for their antioxidant properties. Their disadvantage for protein formulation is limited solubility. Their ability to preserve EP0-D11 binding upon exposure to UV radiation was measured. Formulations of EPO (40 kU/mL), 25 mM sodium phosphate, 125 mM sodium chloride, and 0.005% Tween-80 at pH 6.90 were prepared in the presence or absence of 20 mM catechin. After exposure to 0-8 hours UV radiation, the percent binding of EPO to D11 was measured (FIG. 27), and catechin was able to preserve EPO binding.

Figure 28:
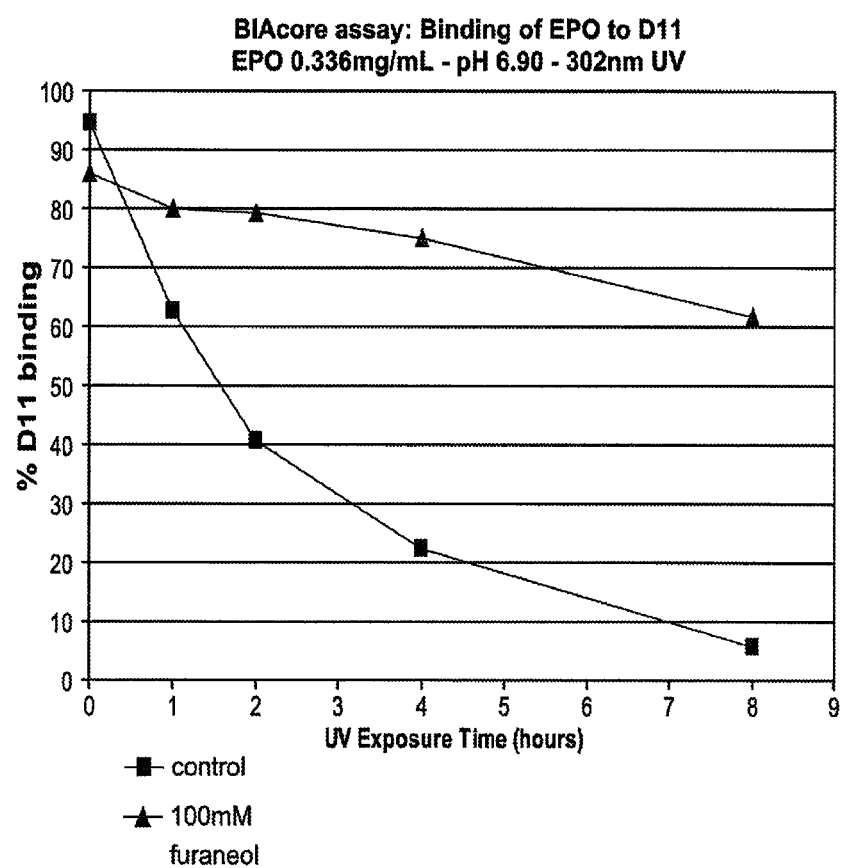
FIG. 28 shows binding of EP0 to D11, in formulations containing no antioxidant or 100 mM furaneol, after exposure to UV radiation for 0-8 hours.

Furaneol is the compound which gives strawberries their flavor and aroma. It is present in other fruits as well in lower amounts and is added to foods and drinks as a natural and artificial flavor. FIG. 28 shows that a formulation of 100 mM furaneol in a formulation of 40 kU/mL EPO, 25 mM sodium phosphate, 125 mM sodium chloride, and 0.005% Tween-80 at pH 6.90 is able to protect EPO binding to D11 after exposure to 0-8 hours UV radiation at 4° C.

Example 15

Effect of Sulisobenzone on Binding Activity of Therapeutic Proteins

Figure 29:
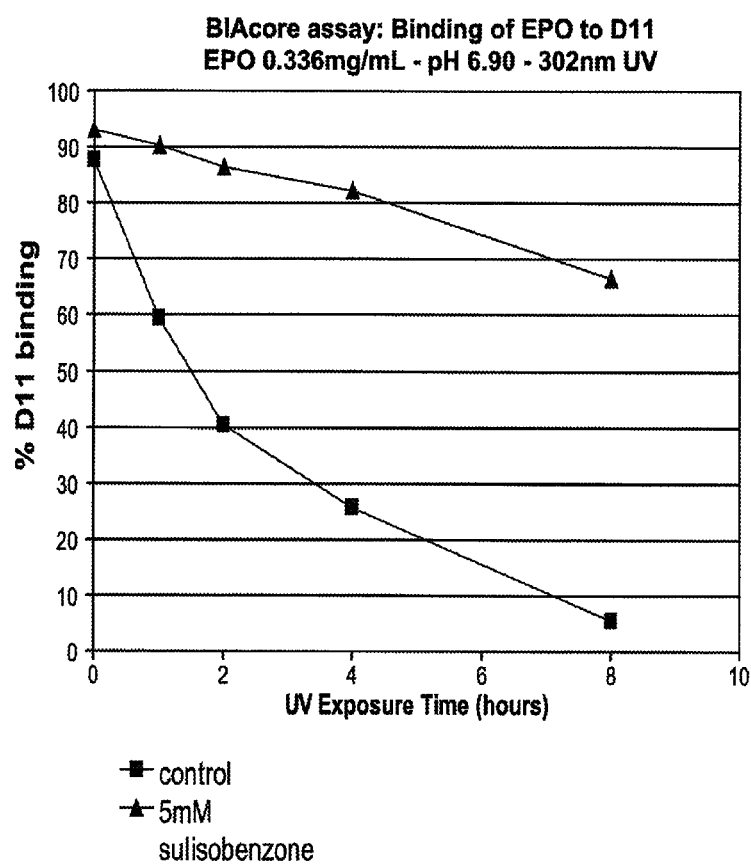
FIG. 29 shows binding of EP0 to D11, in formulations containing no antioxidant or 5 mM sulisobenzone, after exposure to UV radiation for 0-8 hours.

Sulisobenzone is a component in many sunscreens. FIG. 29 shows that a formulation of 5 mM sulisobenzone with 40 kU/mL EPO, 25 mM sodium phosphate, 125 mM sodium chloride, and 0.005% Tween-80 at pH 6.90 is able to protect EPO binding to D11 after exposure to 0-8 hours UV radiation at 4° C.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed:

1. An aqueous formulation suitable for parenteral administration comprising an erythropoiesis stimulating protein, wherein the erythropoiesis stimulating protein is a protein that is 90% or more identical in amino acid sequence to human erythropoietin (SEQ ID NO: 1) or darbepoetin (SEQ ID NO: 2), and a stabilizing concentration of an antioxidant, wherein the antioxidant is syringic acid and wherein the antioxidant is present in the aqueous formulation at a concentration of about 0.1 mM to about 20 mM.

2. An aqueous formulation suitable for parenteral administration comprising an erythropoiesis stimulating protein, wherein the erythropoiesis stimulating protein is a protein that is 90% or more identical in amino acid sequence to human erythropoietin (SEQ ID NO: 1) or darbepoetin (SEQ ID NO: 2), and a stabilizing concentration of an antioxidant, wherein the antioxidant is selected from the group consisting of coumaric acid, ferulic acid, and sinapic acid, and wherein the antioxidant is present in the aqueous formulation at a concentration of about 0.1 mM to about 20 mM.

3. An aqueous formulation suitable for parenteral administration comprising an erythropoiesis stimulating protein, wherein the erythropoiesis stimulating protein is a protein that is 90% or more identical in amino acid sequence to human erythropoietin (SEQ ID NO: 1) or darbepoetin (SEQ ID NO: 2), and a stabilizing concentration of an antioxidant, wherein the antioxidant is selected from the group consisting of furaneol and sulisobenzone, and wherein, when the antioxidant is furaneol, the antioxidant is present in the aqueous formulation at a concentration of about 0.1 mM to about 300 mM and when the antioxidant comprises sulisobenzone, the antioxidant is present in the aqueous formulation at a concentration of about 0.1 mM to about 300 mM.

4. The aqueous formulation of claim 1, 2 or 3, wherein the erythropoiesis stimulating protein comprises erythropoietin (SEQ ID NO: 1) or darbepoetin (SEQ ID NO: 2).

5. The aqueous formulation of claim 1, 2 or 3, wherein the erythropoiesis stimulating protein has a concentration of about 0.001 to about 1 mg/mL.

6. The aqueous formulation of claim 1, 2 or 3, wherein the erythropoiesis stimulating protein exhibits less than about 10% degradation of the protein as determined by exposure for about 3 hours to a 8 watt mid UV lamp having a spectral distribution from 270 nm to 360 nm with a maximum energy emission of about 302 nm.

7. The aqueous formulation of claim 1, 2 or 3, wherein the erythropoiesis stimulating protein exhibits less than 2% degradation.

8. The aqueous formulation of claim 1, 2 or 3, further comprising an osmolyte.

* * * * *

SEQUENCE LISTING

```
<160> NUMBER OF SEQ ID NOS: 2

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80
```

```
Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135             140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 165
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Asn Glu Thr
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Val Asn Glu Thr Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
            130                 135             140

Tyr Ser Asn Phe Leu Arg Gly Lys Leu Lys Leu Tyr Thr Gly Glu Ala
145                 150                 155                 160

Cys Arg Thr Gly Asp
                165
```